(12) United States Patent
Block et al.

(10) Patent No.: US 9,241,502 B2
(45) Date of Patent: Jan. 26, 2016

(54) ANIMAL FEED COMPOSITIONS CAPABLE OF REDUCING THE INCIDENCE OF FESCUE TOXICOSIS IN MAMMALS

(75) Inventors: Stephanie S. Block, Decatur, IN (US); Michael J. Cecava, Decatur, IN (US); Perry H. Doane, Decatur, IN (US)

(73) Assignee: ADM Alliance Nutrition, Decatur, IN (US)

( * ) Notice: Subject to any disclaimer, the term of this patent is extended or adjusted under 35 U.S.C. 154(b) by 1579 days.

(21) Appl. No.: 11/340,172

(22) Filed: Jan. 26, 2006

(65) Prior Publication Data

US 2006/0188549 A1    Aug. 24, 2006

Related U.S. Application Data

(60) Provisional application No. 60/648,050, filed on Jan. 28, 2005.

(51) Int. Cl.

| | |
|---|---|
| A61K 36/81 | (2006.01) |
| A23K 1/00 | (2006.01) |
| A23K 1/14 | (2006.01) |
| A23K 1/16 | (2006.01) |
| A23K 1/17 | (2006.01) |
| A23K 1/18 | (2006.01) |
| A61K 35/74 | (2015.01) |
| A61K 36/185 | (2006.01) |
| A61K 45/06 | (2006.01) |
| A61K 36/67 | (2006.01) |

(52) U.S. Cl.
CPC . *A23K 1/009* (2013.01); *A23K 1/14* (2013.01); *A23K 1/1603* (2013.01); *A23K 1/1612* (2013.01); *A23K 1/1634* (2013.01); *A23K 1/17* (2013.01); *A23K 1/1813* (2013.01); *A61K 35/74* (2013.01); *A61K 36/185* (2013.01); *A61K 36/67* (2013.01); *A61K 36/81* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 4,755,519 A | * | 7/1988 | Dougherty et al. .......... 514/276 |
| 4,939,149 A | | 7/1990 | Blumberg |
| 5,558,889 A | | 9/1996 | Rossi |
| 5,874,102 A | | 2/1999 | LaJoie et al. |
| 5,879,696 A | | 3/1999 | Blumberg |
| 5,935,623 A | | 8/1999 | Alonso-Debolt |
| 6,045,834 A | | 4/2000 | Howes et al. |
| 6,344,221 B1 | * | 2/2002 | Evans ........................ 426/2 |
| 6,616,962 B1 | | 9/2003 | Fernandez |

FOREIGN PATENT DOCUMENTS

| | | | |
|---|---|---|---|
| JP | 2002330734 | | 11/2002 |
| WO | WO 99/59430 | * | 11/1999 |
| WO | WO 02/085132 A1 | | 10/2002 |

OTHER PUBLICATIONS

Gillespie, Vasodilator Properties of Alcohol, 1967, Brit. Med. J., vol. 2, pp. 274-277.*
Heitzer et al., Effect of vitamin E on endothelial vasodilator function inpatients with hypercholesterolemia, chronic smoking or both, 1999, J. Am. Coll. Cardiol., vol. 33, pp. 499-505.*
Solomons et al., Reactivity of dorsal pedal vein of cattle to selected alkaloids associated with Acremonium coenophialum-infected fescue grass, 1989, Am J Vet Res, 50, 235-238.*
Prieto et al., Calcitonin gene-related peptide is a potent vasodilator of bovine retinal artieries in vitro, 1991, Exp Eye Res, 53, 399-405.*
Saito, Evaluation of the Nitrogen-fixing ability of endophyte clostridia based on acetylene reduction and reverse transcription-PCR trageting the nifH Transcript and Ribosomal RNA, 2006, Microbes and Environments, 21, 23-35.*
Peters et al., Performance, Forage Utilization, and Ergovaline Consumption by Beef Cows Grazing Endophyte Fungus-Infected Tall Fescue, Endophyte Fingus-free Tall Fescue, or Orchardgrass Pastures, 1992, J Anim Sci, 70, 1550-1561.*
Larson et al., Effects of Niacin and Apsirin on the Performance Parameters in Heifers Fed Endophyte Infected Tall Fescue, 1992, J Anim Sci, 70: 22.*
Plantmanagementnetwork http://www.plantmanagementnetwork.org/pub/cm/management/2004/toxicosis/.*
Netpets https://www.netpets.org/horses/healthspa/grass.html.*
Cardozo, P.W. et al., "Effects of natural plant extracts on ruminal protein degradation and fermentation profiles in continuous culture." Journal of Animal Science, 2004, 82: 3230-3236.
"Food and Drugs" 21 C.F.R. §582.1 and §582.10 (1998).
"Ketonic" in Agri Dynamics marketing pamphlet, available at www.agri-dynamics.com (last visited Feb. 5, 2007).
"Hemocel 100" in Agri Dynamics marketing pamphlet, available at www.agri-dynamics.com (last visited Feb. 5, 2007).
"Aqua-Flo Capsules" in Agri Dynamics marketing pamphlet, available at www.agri-dynamics.com (last visited Feb. 5, 2007).
"Dyna-Vites" in Agri Dynamics marketing pamphlet, available at www.agri-dynamics.com (last visited Feb. 5, 2007).
Gadberry, M.S. et al., "Effects of feeding ergovaline on lamb performance in a heat stress environment." Journal of Animal Science, 2003, 81:1538-1545.
Hill, N.S. et al., "Ergot alkaloid transport across ruminant gastric tissues." Journal of Animal Science, 2001, 79:542-549.
Jackson, J.A. et al., "Effect of Dietary Supplementation with Vitamin E for Lactating Dairy Cows Fed Tass Fescue Hay Infected with Endophyte." Journal of Dairy Science, 1997, 80:569-572.

(Continued)

Primary Examiner — Terry A McKelvey
Assistant Examiner — Catheryne Chen
(74) Attorney, Agent, or Firm — Andrew F. Nilles

(57) ABSTRACT

Animal feed compositions having utility in reducing the incidence of and treating the symptoms of fescue toxicosis in mammals that consume endophyte-infected fescue are disclosed. Methods of reducing the incidence of fescue toxicosis and making animal feed compositions are further disclosed.

24 Claims, 2 Drawing Sheets

(56) References Cited

OTHER PUBLICATIONS

Oliver, J.W. et al., "Vasoconstriction in Bovine Vasculature Induced by the Tall Fescue Alkaloid Lysergamide." *Journal of Animal Science*, 71:2708-2713.

Chestnut, A.B. et al., "Effects of Hydrated Sodium Calcium Aluminosilicate on Fescue Toxicosis and Mineral Absorption." *Journal of Animal Science*, 1992, 70:2838-2846.

Samford-Grigsby M.D. et al., "Injection of a Dopamine Antagonist into Holstein Steers to Relieve Symptoms of Fescue Toxicosis." *Journal of Animal Science*, 1997, 75:1026-1031.

Filipov, N.M. et al., "Vaccination Against Ergot Alkaloids and the Effect of Endophyte-Infected Fescue Seed-Based Diets on Rabbits." *Journal of Animal Science* 1998, 76:2456-2463.

Ilsley, S.E. et al., "Plant extracts for sows and suckling piglets." *Feed Mix*, 12(4), 2004, 24-27.

Ilsley, S.E. et al., "Plant Extracts as supplements for lactating sows: effects on piglet performance, sow food intake and diet digestibility." *Animal Science*, 2003, 77:247-254.

Hill N.S. et al., "Urinary alkaloid extraction as a diagnostic tool for fescue toxicosis in cattle." *J. of Vet. Diagn. Invest.*, 2000,12(3):210-217.

Simeone A. et al., "Comparison of two ammoniation procedures to reduce the toxicity of endophyte-infected tall fescue seed fed to rats." *Drug Chemi Toxicol.* 1998, 21(3):387-404.

Zygmunt, P.M. et al., "Vanilloid receptors on sensory nerves mediate the vasodilator action of anandamide." *Nature*, 1999, 400(6743):452-45.

Akay, V. et al., "Supplementation of FEB-200 to alleviate endophyte toxicosis in steers." *Journal of Animal Science*, 2003 81(Suppl. 1);229 (Abstract M207).

Ilsley, S. et al., "Herbal sow diets boost preweaning growth." *Pig Progress*, 18(4), 2002, 8-11.

"XTRACT From research to commercial success," in P&A Marketing News vol. 3, No. 1, 2003, 4-5, available at http://www.pancosma.com/pdf/News03.pdf (last visited Mar. 15, 2006).

Marketing pamphlet entitled "XTRACT: When Performance Comes Naturally," distributed by Pancosma & Associates Marketing, Switzerland, available at www.pancosma.com/pdf/axiss4.pdf (last visited Mar. 15, 2006).

Ilsley, S. et al., "Herbal sow diets boost preweaning growth." *Feed Mix*, 10(3), 2002, 24-25.

Kamel, C. "Natural Plaint Extracts: Classical Remedies Bring Modern Animal Production Solutions. In Feed Manufacturing in the Mediterranean Region." *Mediterranean Agronomic Institutes*, 2001, pp. 31-38.

Vanner, S. et al., "Submucosal Secretomotor and Vasodilator Reflexes." *Neurogastroenterol Motil* (2004) 16 Suppl. 1), 39-43.

Zayachkivska, O. S., et al., "Gastroprotective Effects of Flavonoids in Plant Extracts." *Journal of Physiology and Pharmacology* 2005, 56, Suppl. 1, 219-231.

Gangula, P.R.R. et al., "Mechanisms Involved in Calcitonin Gene-Related Peptide-Induced Relaxation in Pregnant Rat Uterine Artery." *Biology of Reproduction* 69, 1635-1641 (2003).

Klukovits, A., et al., "Role of Capsaicin-Sensitive Nerve Fibers in Uterine Contractility in the Rat." *Biology of Reproduction* 70, 184-190 (2004).

Surh, Y-J, et al., "Capsaicin, A Double-Edged Sword: Toxicity, Metabolism, and Chemopreventive Potential." *Life Sciences*, vol. 56, No. 22, pp. 1845-1855, 1995.

Jamroz, D. et al., "Use of Active Substances of Plant Origin in Chicken Diets Based on Maise and Locally Grown Cereals." *British Poultry Science*, Aug. 2005; 46(4): 485-93.

Van Eijndhoven, H.W.F. et al., "Vasodilator Reactivity to Calcitonin Gene-Related Peptide is increased in Mesenteric Arteries of Rats During Early Pregnancy." *Journal of Vascular Research*, J Vas Res 2003; 40:344-350.

Nagy, I. et al., "The Role of the Vanillold (Capsaicin) Receptor (TRPV1) in Physiology and Pathology." *European Journal of Pharmacology* 500 (2004) 351-369.

Atkinson, M., "The Effects of Prenatal Capsaicin on the Distribution of Substance P in Developing Primary Afferent Neurons." *Neuroscience Letters*, 35 (1983) 25-29.

Surh, Y.-J, et al., "Metabolism of Capsaicinoids: Evidence for Aliphatic Hydroxylation and its Pharmacological Implications." *Life Sciences*, vol. 56, No. 16 pp. PL 305-311, 1995.

Manzini, S. et al., "Vascular Effects of Capsaicin in Isolated Perfused Rat Mesenteric Bed." *European Journal of Pharmacology*, Mar. 29, 1988; 148 (2):153-9.

Gourine, A. et al., "Role of Capsaicin-Sensitive Afferents in Fever and Cytokine Responses During Systemic and Local Inflammation in Rats." *NeuroImmunoModulation*, 2001; 9(1): 13-22.

Gibbins, I.L. et al., "Co-Localization of Calcitonin Gene-Related Peptide-Like Immonoreactivity With Substance P in Cutaneous, Vascular and Visceral Sensory Neurons of Guinea Pigs." *Neuroscience Letters*, Jun. 12, 1985; 57(2): 125-30.

Vaishnava, P. at al., "Capsaicin Sensitive-Sensory Nerves and Blood Pressure Regulation." *Curr. Med. Chem.—Cardiovasc. Hematological Agents*, Jun. 2003; 1(2): 177-88.

Mejia, J. et al., "Effects of Neuropeptide Y, Calcitonin Gene-Related Peptide, Substance P, and Capsaicin on Cerebral Arteries in Man and Animals." J. Neurosurg. 1988: 69(6): 913-8.

Dib, B. et al., "Rats Desensitized by Capsaicin Alter Their Food Intake Regulation Especially at Cold Ambient Temperature." *Drugs Exptl. Clin. Res.*, 2005; 31(2):53-8.

Van De Wall, E. et al., "Deafferentation Affects Short-Term But Not Long-Term Control of Food Intake." *Physiology & Behavior*, Mar. 31, 2005; 84(4): 659-67.

Cabanac, M. et al., "The Effect of Capsaicin on Temperature Regulation of the Rat." *Pflügers Archiv.*, Nov. 5, 1976: 366(2-3): 217-21.

Jensen, P. et al., "Field Evaluation of Capsaicin as a Rodent Aversion Agent for Poultry Feed." *Pest Management Science*, Sep. 2003: 59(9): 1007-15.

McElroy, A. et al., "Effect of Prolonged Administration of Dietary Capsaicin on Broiler Growth and *Salmonella enteritidis* Susceptibility." *Avian Diseases*, 1994; 38(2): 329-33.

Rhodes, M.T., et al., "Reduced Blood Flow to Peripheral and Core Body Tissues in Sheep and Cattle Induced by Endophyte-Infected Tall Fescue," *Journal of Animal Science*, 1991, 69:2003-2043.

International Search Report for International Application No. PCT/US2006/004870, European Patent Office (acting as International Searching Authority), 4 pages, Jun. 19, 2006.

Written Opinion of the International Searching Authority for International Application No. PCT/US2006/004870, European Patent Office (acting as International Searching Authority), 6 pages, Jun. 19, 2006.

J.A. Stuedemann, F.N. Thompson, "Pathophysiology of fescue toxicosis," Agriculture, Ecosystems and Environment, 44, 1993, p. 263-281.

Chen, H.Y., "Recent advances in Nutrition of Penaeus monodon", Journal of the World Aquaculture Society, vol. 24(2), Jun. 1993, pp. 231-240.

Yang H. et al, Effect of adding a mannanoligosacchride product on performance of nursery pigs fed diets with or without antibiotics, J. Animal Science (Suppl 1), Jul. 24-28, 2005, USA.

Smiricky et al, The influence of soy oligosaccharides on apparent and true ileal amino acid digestibilities and fecal consistency in growing pigs, J. Animal Science, pp. 2433-2441, 2002 USA.

ADM, CitriStim Technical Data Sheet, Feb. 2005, USA.

ADM, CitriStim Product Sales Sheet, Feb. 2005, USA.

\* cited by examiner

Each pen (1 or 2) contained both minerals.

Pros. Pen 1=amount of PROSPECTOR® mineral consumed (kg/hd/day) in pen 1.

Fescue Pen 1=amount of experimental fescue mineral consumed (kg/hd/day) in pen 1.

Pros. Pen 2=amount of PROSPECTOR® mineral consumed (kg/hd/day) in pen 2.

Fescue Pen 1=amount of experimental fescue mineral consumed (kg/hd/day) in pen 2.

ical materials which are expensive. Injections lead to
ANIMAL FEED COMPOSITIONS CAPABLE OF REDUCING THE INCIDENCE OF FESCUE TOXICOSIS IN MAMMALS

CROSS REFERENCE TO RELATED APPLICATIONS

This application claims the priority benefit of U.S. Provisional Patent Application No. 60/648,050, filed Jan. 28, 2005, the disclosure of the entirety of which is incorporated by this reference.

TECHNICAL FIELD

The technology relates to feed supplements for reducing the incidence of fescue toxicosis in mammals, and to methods for reducing the incidence of fescue toxicosis in mammals.

BACKGROUND

Tall fescue is a hardy, rangeland grass, which is a primary forage for grazing ruminants, especially during the hot summer months. It is grown on approximately 1.4 million hectares throughout the United States. The ability of tall fescue to withstand temperature extremes is, at least in part, a result of a symbiotic relationship between the plant and an endophytic fungus, *Neotyphodium coenophialum*. It is estimated that greater than 80% of all fescue is infected with the fungus.

Although the symbiosis has advantages for the grass, *N. coenophialum* also produces ergovaline and ergot alkaloids. These naturally occurring chemicals are responsible for fescue toxicosis, a widespread problem affecting both beef and dairy cattle. Data indicates that feeding ruminants ergovaline impairs their performance (Gadberry M. S., Denard T. M., Spiers D. E., Piper E. L., "Effects of feeding ergovaline on lamb performance in a heat stress environment," *J. Anim. Sci.* 2003 June; 81(6):1538-45). Conversion of ergovaline to ergot alkaloids leads to detectable concentrations of alkaloids in the urine, which are correlated with toxicosis symptoms (Hill N. S., Thompson F. N., Stuedemann J. A., Dawe D. L., Hiatt E. E., "Urinary alkaloid extraction as a diagnostic tool for fescue toxicosis in cattle," *J. Vet. Diagn. Invest.* 2000 May; 12(3): 210-7). Absorbed ergovaline and ergot alkaloids cause a reduction in vasoactivity (Oliver J. W., Abney L. K., Strickland J. R., Linnabary R. D., "Vasoconstriction in bovine vasculature induced by the tall fescue alkaloid lysergamide," *J. Anim. Sci.* 1993 October; 71(10):2708-13) and subsequent impairment of heat regulation. Impairment of immune function also is observed. Cattle affected by fescue toxicosis suffer from reduced appetite and growth, impaired reproduction and lactation, and impaired circulation to the extremities, which leads to the inability to dissipate heat during summer heat stress or, in winter, the inability to maintain circulation to the feet and tail. Often tails will turn gangrenous and fall off. In more severe situations, feet also will be affected and lost.

Currently, no dietary intervention is available to effectively prevent or treat fescue toxicosis. Methods such as ammoniation of feedstuffs (Simeone A., Boissonneault G. A., Bush L. P., Mitchell, Jr., G. E., "Comparison of two ammoniation procedures to reduce the toxicity of endophyte-infected tall fescue seed fed to rats," *Drug Chem. Toxicol.* 1998 August; 21 (3):387-404) require additional handling and expense and are not applicable to grazing situations where fescue toxicosis is predominantly observed. The use of vaccines (Filipov N. M., Thompson F. N., Hill N. S., Dawe D. L., Stuedemann J. A., Price J. C., Smith C. K., "Vaccination against ergot alkaloids and the effect of endophyte-infected fescue seed-based diets on rabbits," *J. Anim. Sci.* 1998 September; 76(9):2456-63) or dopamine antagonists (Samford-Grigsby M. D., Larson B. T., Forcherio J. C., Lucas D. M., Paterson J. A., Kerley M. S., "Injection of a dopamine antagonist into Holstein steers to relieve symptoms of fescue toxicosis," *J. Anim. Sci.* 1997 April; 75(4):1026-31) require multiple injections of pharmacological materials which are expensive. Injections lead to high labor and animal handling requirements and place additional stress on animals.

Combinations of mineral clay and yeast cell wall extracts have been used to bind and inactivate ergot alkaloids when admixed with feeds or fed directly to animals (U.S. Pat. No. 6,344,221 B1). Calcined aftapulgite clay (U.S. Pat. No. 5,935,623) or a combination of mineral clay and modified yeast wall extracts (U.S. Pat. No. 6,045,834) have been used to remove mycotoxins from animal feeds. While these compositions and methods may help prevent the introduction of ergot alkaloids into the system of the animal, they do not treat the symptoms of fescue toxicosis such as impaired thermoregulation and impaired immune response that result from absorption of ergovaline and ergot alkaloids.

Thus, feed compositions that limit absorption of ergot alkaloids in digestive systems and/or treat the symptoms of fescue toxicosis in fescue-consuming animals would be of value. Low-cost and non-stressful methods to improve the health and performance of animals consuming endophyte-infected fescue also would be advantageous.

SUMMARY

The present disclosure is directed toward compositions that can be used as an additive or supplement to animal feed. In one embodiment, the compositions may be used to reduce the incidence and treat the symptoms of fescue toxicosis in mammals that consume endophyte-infected fescue. The disclosure also includes various methods of making and using the compositions disclosed herein, as set forth below.

In one embodiment, the present disclosure comprises an animal feed composition comprises a coated or encapsulated plant extract consisting of a vasodilator and an ingredient selected from the group consisting of feed matter, a mineral, a vitamin, an amino acid, an antibiotic, and combinations of any thereof.

In another embodiment, the present disclosure comprises a method for feeding an animal. The method comprises mixing a vasodilator with an animal feed product selected from the group consisting of feed matter, a mineral, a vitamin, an amino acid, an antibiotic, a plant extract, a plant botanical, and combinations of any thereof, thus producing an animal feed composition or animal feed supplement. The method further comprises feeding the animal feed composition or animal feed supplement to an animal that may consume endophyte-infected fescue grass, such as, animals selected from the group consisting of bovines, equines, ovines, caprines, or a mixed group of animals comprising any of these.

In a further embodiment, the present disclosure comprises a method for feeding an animal. The method comprises mixing a vasodilator with an animal feed product selected from the group consisting of feed matter, a mineral, a vitamin, an amino acid, an antibiotic, a plant extract, a plant botanical, and combinations of any thereof, thus producing an animal feed composition or animal feed supplement. The method further comprises feeding the animal feed composition or animal feed supplement to a bovine.

In yet another embodiment, the present disclosure comprises an animal feed composition comprising a coated or encapsulated capsaicin containing product; and at least one of a yeast product, a yeast culture, a yeast culture presscake, a citric acid yeast culture presscake, an ethanol yeast culture presscake, a spray dried yeast culture, a spray dried bacterial culture, a yeast extract, a modified yeast extract, a yeast enzyme, and a bacterial enzyme.

In yet a further embodiment, the present invention comprises compositions for consumption by a mammal. The compositions of this embodiment comprise at least one of an adsorbent and an oligosaccharide; and at least one of an antioxidant and a vasodilator. In certain embodiment, the adsorbent may comprise a clay. In other embodiments, the oligosaccharide may comprise one of a yeast product and a yeast culture. In other embodiments, the antioxidant may comprise vitamin E. In other embodiments, the vasodilator may comprise capsicum, which may be coated or encapsulated. The compositions of this embodiment may comprise combinations of the components. In one embodiment, the composition comprises one of the following combinations of components: an adsorbent, an antioxidant, and a vasodilator; an oligosaccharide, an antioxidant, and a vasodilator; an adsorbent, an oligosaccharide, and an antioxidant; and an adsorbent, an oligosaccharide, and a vasodilator.

DETAILED DESCRIPTION

Figure 1:
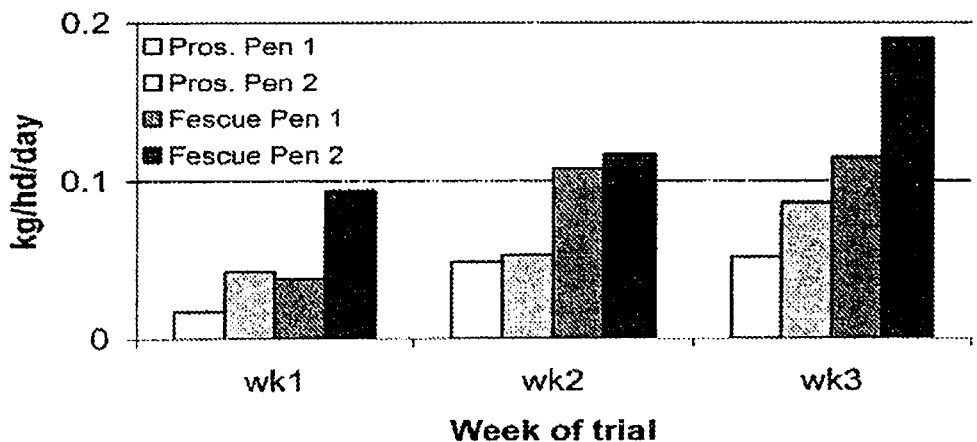
FIG. 1 is a graph showing consumption of one composition according to a non-limiting embodiment disclosed herein in meal form compared to a commercially available feed composition.

In one embodiment, the present disclosure comprises compositions for consumption by a mammal. The compositions may comprise at least one of an adsorbent and an oligosaccharide; and at least one of an antioxidant and a vasodilator. In certain embodiments, the adsorbent may comprise a clay. In other embodiments, the oligosaccharide may originate from at least one of a yeast product and a yeast culture. In other embodiments, the antioxidant may comprise vitamin E. In other embodiments, the vasodilator may comprise capsicum or capsaicin. The compositions of the various embodiments may also comprise combinations of these components. In one embodiment, the composition comprises one of the following combinations of components: an adsorbent, an antioxidant, and a vasodilator; an oligosaccharide, an antioxidant, and a vasodilator; an adsorbent, an oligosaccharide, and an antioxidant; and an adsorbent, an oligosaccharide, and a vasodilator.

In another embodiment of the present invention, the compositions for consumption by a mammal comprise at least one of about 2% to about 99.5% by weight of an adsorbent and about 20% to about 99.5% by weight of an oligosaccharide; and at least one of about 0.5% to about 10% by weight of an antioxidant and about 0.005% to about 1.0% by weight of a vasodilator.

In a further embodiment, the compositions for consumption by a mammal comprise about 2% to about 79% by weight of an aluminosilicate clay; about 20% to about 90% by weight of a yeast product; about 0.5% to about 10% by weight of vitamin E; and about 0.005% to about 1.0% by weight of capsicum. In another embodiment, the composition comprises about 5% to about 50% by weight of the aluminosilicate clay; about 40% to about 90% by weight of the yeast product; about 1.0% to about 5.0% by weight of vitamin E; and about 0.005% to about 0.5% by weight of capsicum. In yet another embodiment, the composition comprises about 10.84% by weight of the aluminosilicate clay; about 86.61% by weight of the yeast product; about 2.45% by weight of vitamin E; and about 0.09% by weight of capsicum, wherein the yeast product comprises 17.3% of a dried yeast on a corn germ carrier.

In another embodiment, the present invention comprises a method of reducing the incidence of fescue toxicosis in a mammal. The method comprises feeding to the mammal a composition comprising at least one of an adsorbent and an oligosaccharide; and at least one of an antioxidant and a vasodilator. In certain embodiments, the composition may be fed to the mammal as a feed supplement, a feed additive, a loose meal, a liquid, a cube, a cooked tub, a mineral, an agglomeration, and a pressed tub.

In yet another embodiment, the present invention comprises a method for the prophylactic treatment of fescue toxicosis in a mammal. The method comprises feeding to the mammal a composition comprising at least one of an aluminosilicate clay and a yeast product; and at least one of vitamin E and capsicum. In another embodiment, the method comprises feeding the mammal a composition comprising the aluminosilicate clay, the yeast product, the vitamin E, and the capsicum, wherein the aluminosilicate clay comprises about 2% to about 79% by weight of the composition; the yeast product comprises about 20% to about 90% by weight of the composition; the vitamin E comprises about 0.5% to about 10% by weight of the composition; and the capsicum comprises about 0.005% to about 1.0% by weight of the composition.

In still another embodiment, the present invention comprises a method of maintaining performance and appropriate body temperature in a mammal during periods when endophyte-infected fescue is consumed by the mammal. The method comprises feeding to the mammal a composition comprising at least one of an aluminosilicate clay and a yeast product; and at least one of vitamin E and capsicum.

In a further embodiment, the present invention comprises a method of making a composition for the prophylactic treatment of fescue toxicosis. The method comprises mixing a composition comprising at least one of an adsorbent and an oligosaccharide, and at least one of an antioxidant and a vasodilator; and forming the composition into one of a feed supplement, a feed additive, a loose meal, a liquid, a cube, a cooked tub, a mineral, an agglomeration, and a pressed tub. In certain embodiments, the method comprises mixing a composition comprising the adsorbent that comprises an aluminosilicate clay; the oligosaccharide that comprises a yeast product; the antioxidant that comprises vitamin E; and the vasodilator that comprises capsicum, wherein the aluminosilicate clay comprises about 2% to about 79% by weight of the composition; the yeast product comprises about 20% to about 90% by weight of the composition; the vitamin E comprises about 0.5% to about 10% by weight of the composition; and the capsicum comprises about 0.005% to about 1.0% by weight of the composition.

It has been determined that mixtures comprising at least one of an adsorbent and an oligosaccharide, and at least one of an antioxidant and a vasodilator can be used as an additive or supplement to animal feed to reduce the incidence and treat the symptoms of fescue toxicosis in mammals that consume endophyte-infected fescue. Certain embodiments of the methods and compositions of the present disclosure comprise an adsorbent and at least one of an antioxidant and a vasodilator. Other embodiments of the methods and compositions of the present disclosure comprise an oligosaccharide and at least one of an antioxidant and a vasodilator. Further embodiments of the methods and compositions of the present disclosure comprise an adsorbent, an oligosaccharide and at least one of an antioxidant and a vasodilator. The present disclosure also includes various methods for reducing the incidence of fescue toxicosis in a mammal and methods for the prophylactic treatment of fescue toxicosis in a mammal, comprising feeding the mammal the compositions of the present disclosure. The present disclosure also includes method of making the various compositions of the present disclosure.

Certain individual components of the various embodiments of compositions of the present disclosure may improve the health and performance of animals consuming endophyte-infected fescue. Adsorbent clays such as hydrated sodium calcium aluminosilicate are able to bind ergot alkaloids in vitro (Chestnut A. B., Anderson, P. D., Cochran, M. A., Fribourg, H. A., Gwinn, K. D., "Effects of hydrated sodium calcium aluminosilicate on fescue toxicosis and mineral absorption," *J. Anim. Sci.,* 1992 September 70(9):2838-2846). However, animal data demonstrating improved performance on feeding animals such clays are minimal. Modified yeast cell wall products have been proposed to reduce the severity of toxicosis (Akay, V., Foley, M., Jackson, J. A., Kudopoje, M., Dawson, K. A., "Supplementation of FEB-200 to alleviate endophyte toxicosis in steers," *J. Anim. Sci.,* 2003 81 (Suppl. 1); 229 (Abstract M207)). Vitamin E was evaluated in lactating dairy cattle and as a single ingredient was not found to be effective against fescue toxicosis (Jackson, J. A., Harmon, R. J., Tabeidi, Z., "Effect of dietary supplementation with vitamin E for lactating dairy cows fed tall fescue hay infected with endophyte," *J. Dairy Sci.,* 1997 80:569-572). Finally, vasoactivity can be affected by capsaicin acting through vanilloid receptors to induce vasodilation and subsequently improve ability to dissipate heat (Zygmunt, P. M., Petersson, J., Andersson, D. A., Chuang, H., Sogard, M., DiMarzo, V., Julius, D., Hogestaft, E. D., "Vanilloid receptors on sensory nerves mediate the vasodilator action of anandamide," *Nature,* 1999 Jul. 29; 400(6743):452-457).

The incorporation of various components into a feed additive or a feed supplement, as disclosed herein, presents a novel approach for the treatment of fescue toxicosis. The methods and compositions of the present disclosure are designed to improve digestive system function, bind toxins, support immune function, and improve the ability to dissipate heat for animals that consume endophyte-infected fescue forage and/or suffer from fescue toxicosis.

Other than in the operating examples, or where otherwise indicated, all numbers expressing quantities of ingredients, reaction conditions and the like used in the specification and claims are to be understood as being modified in all instances by the term "about". Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques. All values reported in percentages are reported as weight percentages, unless specifically denoted otherwise.

Notwithstanding that the numerical ranges and parameters setting forth the broad scope of the invention are approximations, the numerical values set forth in the specific examples are reported as precisely as possible. Any numerical values, however, inherently contain certain errors necessarily resulting from the standard deviation found in their respective testing measurements.

Also, it should be understood that any numerical range recited herein is intended to include all sub-ranges subsumed therein. For example, a range of "1 to 10" is intended to include all sub-ranges between (and including) the recited minimum value of 1 and the recited maximum value of 10, that is, having a minimum value equal to or greater than 1 and a maximum value of equal to or less than 10.

Certain non-limiting embodiments of the compositions of the present disclosure may comprise an adsorbent. The term "adsorbent", as used herein, is defined as a composition that has the ability to adsorb water and certain organic compounds, including but not limited to, aflatoxin, ergovaline, and ergot alkaloids. Adsorbents suitable for use in certain non-limiting embodiments of the present disclosure include, but are not limited to, activated carbon and clay minerals. The term "activated carbon", as used herein, is defined as including any of the number of compositions made primarily of adsorbent carbon in lump, pellet, granular, or powder form, including, but not limited to, any of the compounds under the terms "activated charcoal", "active carbon", "active charcoal", "amorphous carbon", "bone black", "bone coal", "charcoal black", "charcoal", "decolorizing carbon", and "lamp black". The terms "clay minerals", "mineral clay" or "clay", as used herein, are defined as any of a complex group of finely crystalline to amorphous, essentially hydrated aluminum silicate minerals of tectosilicate and phyllosilicate origin having the generalized formula $Al_2O_3SiO_2.xH_2O$, characterized by small particle size, cation exchange capability, and/or the ability to adsorb water and certain organic compounds, such as, but not limited to, aflatoxin, ergovaline, and ergot alkaloids. Minerals and vitamins may also be adsorbed to these clays. The most common mineral clays belong to the kaolinite, smectite, allophone, vermiculite, interstratified clays and illite groups including, but not limited to, the montmorillonite, attapulgite and bentonite groups. The terms "clay minerals", "mineral clay" or "clay" may also include, but is not limited to, natural tectosilicate minerals of the zeolite group and the synthetic zeolites or sodium calcium silicoaluminates. The term "aluminosilicate clay", as used herein, is defined as comprising a combination of silicate and aluminate in the form of a mineral clay. The term "kaolinite", as used herein, is defined as one member of the group of common aluminosilicate clays.

Activated carbon may be used in certain non-limiting embodiments of the composition of the present disclosure in either lump, pellet, granular, or powder form. Examples of suitable activated carbon compositions include, but are not limited to, CALGON™ (available from the Calgon Carbon Corp. of Pittsburgh, Pa.) and TOXIBAN® (available from Vet-a-Mix of Shenandoah, Iowa).

Aluminosilicate clays that may be used in certain non-limiting embodiments of the composition of the present disclosure may be any of a number of standard commercial grade aluminosilicate clays suitable for inclusion in animal diets. Aluminosilicate clays may be obtained from a variety of commercial sources. Examples of commercially available aluminosilicate clays suitable for use in various compositions of the present disclosure include, but are not limited to, BIO-FIX® (a blend of clay, enzymes and botanicals available from Biomin GmbH in Austria) and NUTRADE® (available from ADM Alliance Nutrition in Quincy, Ill.). Mineral clays in the form of natural and synthetic zeolites suitable for use in certain embodiments of the present disclosure include, but are not limited to, zeolites available from various mining sources, FEED BOND® (available from ACG Products Ltd. of Brookfield, Wis.), ZEOPRO™ (available from ZeoponiX, Inc. of Boulder, Colo.), and ZAR-MIN® (available from Zeo, Inc. of McKinney, Tex.).

Certain non-limiting embodiments of compositions of the present disclosure may also comprise an oligosaccharide. As used herein, the term "oligosaccharide" is defined as a composition comprised, at least in part, of polysaccharides containing from two to about fifty monosaccharide units connected by glycosidic linkages. Oligosaccharides suitable for use in certain non-limiting embodiments of the present disclosure include, but are not limited to, yeast, including yeast dried on a suitable carbohydrate carrier; yeast cultures; algae cultures; bacterial cultures; modified starches; enzymes extracted or isolated from a bacteria, yeast or mold; yeast extracts; modified yeast extracts; spray dried yeast culture, a spray dried bacterial culture; and oligosaccharides, such as, but not limited to, mannanoligosaccharides, fructooligosaccharides, and beta-glucans, isolated from yeast and yeast cultures. Oligosaccharides may also include various combinations of any of the oligosaccharides set forth above.

As used herein, the term "yeast product" means dried, non-fermentative yeast which has been separated from the medium in which it was propagated and dried on a suitable carrier. As used herein, the term "carrier" means an edible material to which yeast is added to facilitate uniform incorporation of the latter into feeds. The active particles are adsorbed, impregnated, or coated into or onto the edible material in such a way as to physically carry the active ingredient. Carriers suitable for use in certain non-limiting embodiments of the present disclosure include, but are not limited to grain germ, such as, for example, corn germ or wheat germ. In certain non-limiting embodiments of the present disclosure, the carrier portion of the yeast product comprises from 0% to 90% by weight of the total weight of the yeast product. In one non-limiting embodiment, the carrier comprises 0% of the weight of the yeast product, such that the yeast product comprises dried, non-fermentative yeast, such as a spray dried yeast, and no carrier. In another non-limiting embodiment, the carrier comprises corn germ and comprises from about 75% to about 90% of the total weight of the yeast product.

As used herein, the term "yeast culture" is defined as the product comprising mycelium of yeast fermentation and the media on which it was grown, such as, for example, a presscake. The yeast culture comprises the enzyme system of the viable organism and its concomitant metabolites produced during the fermentation process and not removed during the separation process. The process of separation includes, but is not limited to, filtration and pressing, and centrifugation. The fermentation process can be, but is not limited to, a penicillium fermentation, a *Streptomyces* fermentation, an ethanol fermentation, or a citric acid fermentation. Yeast organisms useful in the compositions described herein include, without limitation, the *Saccharomyces, Candida, Pichia, Yarrowia, Kluyveromyces*, or *Torulaspora* species. In certain non-limiting embodiments of the present disclosure, the yeast used is *Pichia guilliermondii* or *Yarrowia lipolytica*.

As used herein, the term "presscake" means the filtered or centrifuged; and dried mycelium obtained from separation of the fermentation. The term "citric acid presscake", as used herein, means the filtered or centrifuged; and dried mycelium obtained from a citric acid fermentation using an acceptable aqueous carbohydrate substrate. The term "ethanol presscake" is defined as the filtered or centrifuged mycelium obtained from an ethanol fermentation using an acceptable aqueous carbohydrate substrate. The yeast organism may be made nonviable and may be completely removed from the citric acid or ethanol during the separation and purification process. Citric acid presscakes can be a product resulting from *Pichia* or *Yarrowia* yeast fermentation to produce citric acid, in which case it contains cell walls and cell wall contents with high concentrations of mannanoligosaccharides, fructooligosaccharides, and/or beta-glucans. The oligosaccharides and yeast cultures that may be used in the compositions of the present disclosure may be obtained, for example, from a variety of commercial sources. Non-limiting examples of commercially available oligosaccharide sources, yeasts, yeast products, presscakes, and yeast cultures and extracts suitable for use in the compositions of the present disclosure include, but are not limited to, Yeast Cream, ADM MOS, and CITRISTIM® (*Pichia guilliermondii*, citric acid fermentation cultures available from Archer Daniels Midland, of Decatur, Ill.), NUTRASOUND™ (*Lactobacilli* fermentation culture available from ADM Alliance Nutrition, Inc. of Quincy, Ill.), PROSPONSE® (*Saccharomyces cerevisiae* brewer's yeast, available from ADM Alliance Nutrition, Inc. of Quincy, Ill.), A-MAX® (*S. cerevisiae* brewer's yeast culture available from Vi-cor of Mason City, Iowa), YEASACC® (*S. cerevisiae* yeast culture available from Alltech of Lexington, Ky.), BIOSAF® and PROCREATIN® (*S. cerevisiae* yeast available from LaSaffre Yeast Corp. of Milwaukee, Wis.), LEVUCELL® SC (*S. cerevisiae* yeast available from Lallemand, Inc. of Chicago, Ill.), and DIAMOND V® yeast culture (*S. cerevisiae* yeast culture available from DIAMOND V® of Cedar Rapids, Iowa).

Non-limiting embodiments of the compositions of the present disclosure may also comprise an antioxidant. As used herein, the term "antioxidant" is defined as any of a number of natural or synthetic compounds or nutritional supplements that are purported to prevent free-radical oxidation of cellular material. Examples of antioxidants suitable for use in embodiments of the compositions of the present disclosure include, but are not limited to, a tocopherol containing composition, including any of the E vitamins, any of the A vitamins, vitamin C, coenzyme Q10, alpha lipoic acid, any of the carotenes, and the proanthocyanidins, ethoxyquin, BHT, BHA, as well as herbs and herbal extracts such as thymol, carvacrol, turmeric, rosemary, milk thistle, grape, seaweed, and green tea. As used herein, the term "tocopherol" is defined as any member of the class of mono, di-, and trimethyltocols, and mixtures, combinations, and compositions comprised thereof. As used herein, the terms "vitamin E" and "E vitamins" are defined as including alpha-tocopherol, all other tocopherols, and all tocol and tocotrienol derivatives exhibiting qualitatively the biological activity of alpha-tocopherol, including mixtures, combinations, and compositions comprised thereof. The term "vitamin E containing composition" means any mixture or composition comprising at least one tocopherol or one vitamin E. The tocopherol, vitamin E and/or vitamin E containing compositions useful in the compositions of the present disclosure may be obtained from any of a number of commercial sources. Examples of commercially available tocopherol, vitamin E and/or vitamin E containing compositions suitable for use in the compositions of the present disclosure include, but are not limited to, natural vitamin E, synthetic vitamin E, NUTREON® (a vitamin E product available from Archer Daniels Midland, Co. of Decatur, Ill.) and combinations thereof.

Non-limiting embodiments of the compositions within the present disclosure may also comprise a vasodilator. As used herein, the term "vasodilator" is defined as a compound, substance or drug that causes the blood vessels of an animal to dilate (i.e., increase in cross-sectional diameter). Many methods are available to induce vasodilation, one non-limiting example is by activation of the vanilloid receptors or activation via nitric oxide (NO) pathways. Examples of vasodilators or vanilloid receptor activators suitable for use in certain embodiments of the compositions of the present disclosure include, but are not limited to, capsaicin, dihydrocapsaicin, capsinoid, piperine, vanilloids, zingerone, capsicum, macerated or ground hot peppers, hot pepper extract, berberine, niacin (nicotinamide or nicotinic acid), arginine, other capsicum containing plant materials, and other compounds that lead to the activation of vanilloid receptors. Examples of nitric oxide pathway vasodilators include, but are not limited to, cocoa flavanols. In other embodiments, the vasodilator may be isolated or extracted from the capsicum containing plant materials. Capsaicin is the chemical compound present in peppers that is responsible for the "heat" of those peppers and is known to work as a vasodilator (Zygmunt, P. M., Petersson, J., Andersson, D. A., Chuang, H., Sogard, M., DiMarzo, V., Julius, D., Hogestatt, E. D., "Vanilloid receptors on sensory nerves mediate the vasodilator action of anandamide," Nature, 1999 Jul. 29; 400(6743):452-457). The term "capsicum", as used herein, is defined as an extract of any of the plants of the Genus *Capsicum* sp. which includes peppers such as, but not limited to, *Capsicum anuum, C. frutescans, C. baccatum, C. pubescens*, and *C. chinense*. Capsicum contains about 2% to about 20% (w/w) natural capsaicin and capsaicinoids. Higher percentages may be obtained by enhancing capsicum with synthetic capsaicin. In certain non-limiting embodiments of the compositions of the present disclosure, the vasodilator comprises capsaicin. In other non-limiting embodiments the vasodilator comprises capsicum containing about 2% to about 20% (w/w) natural capsaicin and capsaicinoids. In other non-limiting embodiments, the vasodilator comprises capsicum enhanced with synthetic capsaicin containing 2% to 98% (w/w) total capsaicin and capsaicinoids.

In certain embodiments, the vasodilator, for example, but not limited to, capsaicin or capsicum, may be coated or encapsulated. The coating or encapsulation may be performed such that the coated or encapsulated vasodilator comprises a micro-sized spherical particle. For example according to certain embodiments, the coated or encapsulated vasodilator may comprise micro-sized spherical particles having a size range of 125 microns to 400 microns. According to certain embodiments, the material used to coat or encapsulate the vasodilator may comprise a digestible matrix that is degraded in the intestinal tract of an animal the composition is orally consumed by the animal. In certain embodiments, the material used to coat or encapsulate the vasodilator may comprise a hydrogenated vegetable oil matrix, a hydroxypropyl methyl cellulose, or a combination thereof. According to other embodiments, the vasodilator may be coated or encapsulated by coating the vasodilator with a hydrogenated vegetable oil matrix or granulated with the hydroxypropyl methyl cellulose. In certain embodiments, the coating or encapsulation of the vasodilator may enable a manufacturer or user of an animal feed composition comprising the vasodilator to handle the vasodilator or animal feed composition more safely since certain vasodilators that may be used in the various embodiments of the animal feed compositions, such as, for example, capsaicin and capsicum, may be an irritant to persons handling the vasodilator or feed compositions. In other embodiments, the coating or encapsulation of the vasodilator may make the resulting animal feed composition more palatable to an animal consuming the animal feed composition.

As used herein, the term "feed matter" is used to refer to one or more component of an animal feed and may be a wet or dry component. Non-limiting examples of feed matter may include; corn or a component of corn, such as, for example, corn meal, corn fiber, corn hulls, silage, ground corn, or any other portion of a corn plant; soy or a component of soy, such as, for example, soy meal, soy hulls, soy silage, ground soy, or any other portion of a soy plant; wheat or any component of wheat, such as, for example, wheat meal, wheat fiber, wheat hulls, wheat chaff, ground wheat, wheat germ, or any other portion of a wheat plant; canola or any other portion of a canola plant, such as, for example, canola meal, canola protein, canola hulls, ground canola, or any other portion of a canola plant; sunflower or a component of a sunflower plant; sorghum or a component of a sorghum plant; sugar beet or a component of a sugar beet plant; cane sugar or a component of a sugarcane plant; barley or a component of a barley plant; glycerol; corn steep liquor; a waste stream from an agricultural processing facility; molasses; soy molasses; flax; peanuts; peas; oats; grasses, such as orchard grass and fescue, and alfalfa and/or clover used for silage or hay.

In certain embodiments, the animal feed matter may be mixed with various feed ingredients including, but not limited to, amino acids, such as, for example, lysine, threonine, or others; minerals; vitamins; antibiotics; plant extracts or plant botanicals, such as, for example, milk thistle, seaweed, cinnamon, cinnamaldehyde, carvacrol, quillaja extracts, yucca extract, and eugenol; sugars; and polyalcohols.

The present disclosure also provides a method of ameliorating fescue toxicosis and improving the health and performance of endophyte-infected fescue consuming animals by reducing the amounts of ergovaline converted to ergot alkaloids and/OR reducing the symptoms of fescue toxicosis. In vitro data demonstrates that adsorbents, such as clay, and oligosaccharides, such as those derived from yeast products or yeast cultures, alone or in combination, can reduce the amount of ergovaline converted to ergot alkaloids. By reducing the amount of ergovaline converted to more readily absorbed forms, fewer toxins will be absorbed across the rumen wall into the circulatory system of the animal. This activity, combined with the ability of a clay, such as, for example, an aluminosilicate clay, to adsorb ergovaline and reduce uptake across the gastrointestinal tissues, and the toxin binding capability of the mannanoligosaccharides, fructooligosaccharides, and/or beta-glucans in the yeast product or yeast culture, can reduce the total toxin affecting the animal. The capabilities of the adsorbents and oligosaccharides may be used individually or in combination with each other.

In addition to the gastrointestinal effects of the adsorbents, such as clays, and/or oligosaccharides, such as those derived from yeast products or yeast cultures, non-limiting embodiments of compositions within the present disclosure including an antioxidant and/or a vasodilator may also prevent symptoms associated with fescue toxicosis and reduce the incidence of fescue toxicosis by assisting with thermoregulation and improving immune function. The consumption of a vasodilator counteracts the vasoconstrictive effects of the fescue toxins, improving circulation to the extremities and facilitating heat dissipation. The consumption of oligosaccharides, such as the mannanoligosaccharides, fructooligosaccharides, and/or beta-glucans of yeast products or yeast cultures, aids in proper immune function. In addition, proper immune function may be aided by the consumption of antioxidants such as the tocopherols and/or the E vitamins. Mammals consuming endophyte-infected fescue pasture undergo increased stress and therefore may have a higher antioxidant requirement than animals consuming non-endophyte-infected fescue pasture. The combination of an antioxidant with a vasodilator also improves the ability of the antioxidant to access tissues where it is needed.

Unless otherwise noted, percent values of components of the compositions disclosed in the present disclosure are reported as weight percentage. In one non-limiting embodiment of the present disclosure, the composition comprises at least one of an adsorbent and an oligosaccharide, and at least one of an antioxidant and a vasodilator. In another non-limiting embodiment, the composition comprises an adsorbent, an oligosaccharide, and an antioxidant. In another non-limiting embodiment, the composition comprises an adsorbent, an oligosaccharide, and a vasodilator. In another non-limiting embodiment, the composition comprises an adsorbent, an antioxidant, and a vasodilator. In another non-limiting embodiment, the composition comprises an oligosaccharide, an antioxidant, and a vasodilator. In another non-limiting embodiment, the composition comprises an adsorbent, an oligosaccharide, an antioxidant and a vasodilator.

In another non-limiting embodiment, the composition comprises at least one of about 2% to about 99.5% of an adsorbent and about 20% to about 99.5% of an oligosaccharide; and at least one of about 0.5% to about 10% of an antioxidant; and about 0.005% to about 10% of a vasodilator. In another non-limiting embodiment, the composition comprises at least one of about 5% to about 50% of an adsorbent and about 40% to about 90% of an oligosaccharide; and at least one of about 1.0% to about 10% of an antioxidant; and about 0.005% to about 0.5% of a vasodilator.

In another non-limiting embodiment, the composition comprises an adsorbent, an oligosaccharide, an antioxidant and a vasodilator, wherein the adsorbent is an aluminosilicate clay and comprises about 2% to about 79% of the composition; the oligosaccharide is a yeast product and comprises about 20% to about 90% of the composition; the antioxidant is vitamin E and comprises about 0.5% to about 10% of the composition; and the vasodilator is capsicum and comprises about 0.005% to about 0.5% of the composition. In another non-limiting embodiment, the composition comprises about 5% to about 50% of an aluminosilicate clay, about 40% to about 90% of a yeast product, about 1.0% to 5.0% of vitamin E, and about 0.005% to about 0.5% of capsicum. In another non-limiting embodiment, the composition comprises about 10.84% of an aluminosilicate clay; about 86.61% of a yeast product; about 2.45% of vitamin E; and about 0.09% of capsicum, wherein the yeast product comprises 17.3% of a dried yeast on a corn germ carrier. In another non-limiting embodiment where the composition is used as an additive to a feed product and where the yeast product is a spray dried yeast product, the composition may comprise about 0.0026% to about 56.8% of an aluminosilicate clay, about 0.015% to 32.4% of a spray dried yeast product, about 0.005% to 10.5% of vitamin E, and about 0.0002% to about 0.3% of capsicum. For example, in one non-limiting embodiment, the composition comprises 56.8% of an aluminosilicate clay, 32.4% of a spray dried yeast product, 10.5% of vitamin E, and 0.3% of capsicum.

The compositions of the present invention may be fed directly to the animal or as an additive to a feed product. When used as an additive, such as, for example, a premix, in a feed product, the final feed product comprising the additive and animal feed may have a formulation having additive components in sufficient quantities. For example, according to one non-limiting embodiment, when fed as an additive to a final feed, the values (as measured as weight percent of diet or final feed product) for the feed additive components in the final feed may be about 0.0026% to about 56.8% of an aluminosilicate clay, about 0.015% to 32.4% of a spray dried yeast product, about 0.005% to 10.5% of vitamin E, and about 0.0002% to about 0.3% of capsicum.

According to one non-limiting embodiment, where the composition is in the form of a mineral that is mixed with a feed in such a proportion to be fed to an animal at an intake rate of the final feed product of 4 ounces/head/day, the composition of the final feed product may comprise (in weight percent of final feed product) 6.17% of aluminosilicate clay, 3.52% of a spray dried yeast product, 1.15% of vitamin E, and 0.03% of capsicum. According to another non-limiting embodiment where the composition is blended with a feed to give a final feed product, wherein the final feed product intake is 4 pounds feed/head/day, the composition of the final feed product may comprise (in weight percent of final feed product) 0.39% of aluminosilicate clay, 0.22% of a spray dried yeast product, 0.07% of vitamin E, and 0.002% of capsicum. In another non-limiting embodiment where the composition is blended with a feed to give a final feed product, wherein the final feed product intake is 40 pounds/head/day, the composition of the final feed product may comprise (in weight percent of final feed product) 0.039% of aluminosilicate clay, 0.022% of a spray dried yeast product, 0.007% of vitamin E, and 0.0002% of capsicum. One skilled in the art will recognize, based on the present disclosure, that various composition formulations for the final feed product may be calculated based on the initial composition of the additive and the calculated consumption rate for the final feed product by the animal.

The embodiments of compositions within the present disclosure may be fed, for example, as supplements to grazing mammals or may be incorporated into commercially available feeds. When used as a supplement, the compositions of the present disclosure may be ingested by the mammals prior to, during or after grazing or consumption of commercially available feeds.

The physical form of the various non-limiting embodiments of the compositions within the present disclosure may be any suitable formulation known in the feed art. Suitable formulations include, but are not limited to, feed supplement, feed additive, pellet, block, cube, liquid, an agglomeration, mineral, meal, cooked tub, and pressed tub formulations. In one non-limiting embodiment, the physical formulation is a dry, free-flowing loose pellet formulation that is suitable for direct consumption as a supplement or as an additive to feed. In another non-limiting embodiment, the physical formulation is a pressed tub formulation that is suitable for direct consumption by mammals foraging at pasture.

The present disclosure also contemplates various methods of use of the compositions discussed herein. In one embodiment, the present disclosure comprises a method of reducing the incidence of fescue toxicosis in a mammal comprising feeding to the mammal any one of the various non-limiting embodiments of the compositions as described in this disclosure. In another embodiment, the present disclosure comprises a method for the prophylactic treatment of fescue toxicosis in a mammal comprising feeding to a mammal any one of the various non-limiting embodiments of the compositions as described in this disclosure.

As discussed above, mammals that consume endophyte-infected fescue may suffer from decreased performance and increased body temperature due to the inability to dissipate excess body heat, when compared to mammals that consume non-endophyte-infected fescue. In one non-limiting embodiment, the present disclosure comprises a method of maintaining performance and appropriate body temperature in a mammal during periods when endophyte-infected fescue is consumed by the mammal. The method comprises feeding to the mammal any one of the various non-limiting embodiments of the compositions as described and claimed in this disclosure, such as, in one non-limiting embodiment, a composition comprising at least one of an aluminosilicate clay and a yeast product; and at least one of vitamin E and capsicum.

The present disclosure also contemplates methods of making the various non-limiting embodiments of the compositions as disclosed herein. In one non-limiting embodiment, the present disclosure includes a method of making any of the compositions as described herein. The method comprises mixing the components of the composition, for example, in one non-limiting embodiment, mixing at least one of an aluminosilicate clay and a yeast product; and at least one of vitamin E and capsicum. The method further comprises forming the mixed composition into a suitable formulation for consumption by a mammal, for example, but not limited to, a formulation comprising one of feed supplement, feed additive, pellet, block, cube, liquid, an agglomeration, mineral, meal, cooked tub, and pressed tub formulations.

The compositions and methods of the present invention are suitable for treating fescue toxicosis in a variety of mammals exposed to endophyte containing forages, such as ruminants and pasture foraging mammals. The compositions of the present invention can be fed to mammals that may consume endophyte-infected fescue grass, including, but not limited to, bovine, equine, ovine, and caprine species. Generally, the compositions described herein may be fed to any animal, including avian species. Desirable rates of consumption of the compositions are dependant on the mammal age and species; however, target consumption for the various non-limiting embodiments of the compositions may be in the range of between about 10 g/head/day to about 454 g/head/day.

EXAMPLES

The following examples illustrate various non-limiting embodiments of the compositions and methods within the present disclosure and are not restrictive of the invention as otherwise described herein.

Example 1

Ovine Screen

This Example shows the ability of a composition according to one embodiment of the present disclosure to reduce the toxicity of ergovaline-contaminated forages and alleviate the symptoms in ovines. Sixteen male spring lambs (average weight 27.0 kg) were used. Each sheep received one dietary test treatment over a series of environmental conditions. Analysis was conducted using repeated measures analysis with each sheep serving as its own control.

Animals were monitored over a series of environmental and dietary treatments. A basal diet was fed, the test product was added, and after several days, the contaminated fescue diet was substituted for the basal diet. The sheep began the trial under near thermoneutral conditions. Between the addition of test products and the incorporation of fescue toxin, the environmental conditions were altered to induce heat stress.

Diet and environment of the test animals were varied during the test (see Table 1 for description of the treatment periods). During an initial period (Period 1), animals were fed a nutrient preserving technology ("NPT") diet (LGP-4019 diet) (a pellet diet made using Nutrient Preserving Technology as disclosed in U.S. Pat. No. 5,871,802, the contents of which is incorporated herein in its entirety by this reference) formulated to meet their nutrient requirements (see Table 2, showing the composition of the LGP-4019 diet). After 3 days of acclimatization to the housing conditions (study day 4), the products were added to the diet (Period 2: LGP-4019 diet plus additives A, B, C, or D). On day 8 (Period 3: LGP-4019 diet plus additives A, B, C, or D), the temperature was raised to approximately 90° F. and remained at about 90° F. for the rest of the study. Humidity during this period was maintained above 75%. On day 11, diets were changed to an NPT diet containing ergot alkaloid-contaminated fescue seed fed in conjunction with the product (Period 4: LGP-4020 diet plus additives A, B, C, or D) (see Table 2, showing the composition of the LGP-4020 diet). The amount of feed delivered daily and weighbacks were recorded. The additives were ground as necessary and prepared as a powder.

Additive A contained 100% soyhulls.
Additive B contained 50% soyhulls and 50% Clay Blend.
Additive C contained 49.9% soyhulls, 50% Clay Blend, and 0.1% capsicum product.
Additive D contained 46.4% soyhulls, 50% Clay Blend, 3.5% Vitamin E, and 0.1% capsicum product.

TABLE 1

Description of Treatment Periods

| Period | Day of study | Additive | Heat | Toxin |
|---|---|---|---|---|
| Period 1 | 1–3 | No | No | No |
| Period 2 | 4–7 | Yes | No | No |
| Period 3 | 8–10 | Yes | Yes | No |
| Period 4 | 11–22 | Yes | Yes | Yes |

Lambs were fed a pelleted diet containing 20% fescue seed during the study. The control diet (LGP-4019) used ergovaline-free fescue seed (less than 100 ppb ergovaline) while the contaminated diet (LGP-4020) used fescue seed with 2,800 ppb ergovaline. Induction of fescue toxicosis was successfully achieved, using a combination of high heat index and ergovaline-contaminated diet. The complete diet LGP-4020 contained 615 ppb ergovaline, 1041 ppb ergot alkaloids, and no additional ergotamines. Signs of toxicosis were apparent, including reduced feed consumption and weight gain (Table 3—Feed intake and weight gain for test lambs), elevated heart rate (HR), breathing rate (BR), and rectal temperature (RT) (Table 4—Indicators of apparent fescue toxicity in test lambs). Clinical markers of toxicosis also were apparent, such as, a significant reduction in circulating prolactin and numerically increased urinary fescue alkaloid excretion that occurred after the introduction of ergovaline containing feed (Table 5—Clinical markers of fescue toxicity in test lambs). Toxicosis was exclusive to the inclusion of ergovaline-contaminated fescue seed (diet LGP-4020) and did not occur when sheep were fed diets containing an equivalent concentration of the ergovaline-free fescue seed (diet LGP-4019) under identical environmental conditions.

As noted above, the treatment according to this Example was divided into four treatment periods. During period 1, lambs were fed the ergovaline-free control diet (LGP-4019) and allowed to adjust to research conditions and basal observations were collected. Period 2 evaluated the effects of the additives (0.25 lb./head/day) under normal conditions (no heat stress or fescue toxicosis). To ensure complete consumption of the additives, the additive was fed prior to offering the daily allotment of feed. Additives had no effect on any parameter measured during period 2. Period 3 measured the effect of the additives on the lambs during heat stress, without ergovaline-induced toxicity. During this period, RT, HR, and BR increased in all lambs, while feed intake decreased slightly. Period 4 used repeated measurements on each lamb to determine the effect of potential ameliorators on heat stress and ergovaline-induced fescue toxicosis. Room conditions and supplement remained the same during periods 3 and 4; however, during period 4, the base diet was switched to one containing contaminated fescue seed (LGP-4020). In response, serum-prolactin concentration significantly decreased (477 ng/ml to 18 ng/ml), which was not affected by consumption of the additive (Table 5). For most lambs, urinary alkaloids increased from baseline in the second and third collections. The later collections had a high degree of variability between animals and impaired the ability to detect an effect of additive. The inclusion of the additives had no effect on the appearance of alkaloids in the urine (Table 5). In addition, HR, BR, and body temperature increased (Table 4). Rectal temperature tended to be lower in animals consuming the capsicum product and Vitamin E (Additive D) compared with control (104.9° F. vs. 105.3° F., Table 4).

Daily feed intake, compared to control animals consuming soyhulls, was not impaired by the addition of any of the additives. The combination of the capsicum product and Vitamin E was beneficial in reducing body temperature during fescue toxicosis. Due to a lack of effect on prolactin or urinary alkaloids, it appeared that the reduction in body temperature is due to an increase in the ability of the animal to adjust to toxicosis. Of the above additives, additive D was an ameliorator of elevated body temperature induced by fescue toxicosis.

TABLE 2

Composition of Diets

| INGREDIENTS, AS FED | DIET NO. | |
|---|---|---|
| (percent by weight) | LGP-4019 | LGP-4020 |
| CORN, CRACKED | 3.000 | 3.000 |
| CORN, GROUND | 19.099 | 19.099 |
| WHEAT MIDDS | 7.000 | 7.000 |
| ALFALFA, DEHYDRATED | 9.000 | 9.000 |
| SOYHULLS | 12.000 | 12.000 |
| SOYBEAN MEAL | 16.460 | 16.460 |
| VITAMIN AND MINERAL BLEND | 3.841 | 3.841 |
| MOLASSES-CANE | 9.600 | 9.600 |
| ERGOVALINE FREE-FESCUE SEED | 20.000 | — |
| CONTAMINATED-FESCUE SEED | — | 20.000 |
| TOTAL | 100.000 | 100.000 |

| NUTRIENTS | Unit | | | | | | |
|---|---|---|---|---|---|---|---|
| PROTEIN | % | 15.01 | (14.5)[1] | (18.0) | 15.01 | (15.5) | (18.7) |
| FAT; CRUDE | % | 1.56 | (2.3) | | 1.56 | (2.2) | |
| CRUDE FIBER | % | 8.36 | | | 8.36 | | |
| DRY MATTER | % | 86.18 | | | 86.18 | | |
| MOISTURE | % | 13.82 | (9.7) | (10.8) | 13.82 | (9.6) | (8.3) |
| ACID DETERGENT FIBER | % | 10.65 | | (14.0) | 10.65 | | (15.3) |
| TOTAL DIGESTIBLE NUTRIENTS - RUMINANT | % | 54.49 | | | 54.49 | | |
| CALCIUM | % | 0.80 | (0.93) | (0.85) | 0.80 | (0.90) | (1.00) |
| PHOSPHORUS | % | 0.32 | (0.44) | (0.42) | 0.32 | (0.42) | (0.50) |

[1]Analyzed values in parentheses.

TABLE 3

Feed Intake and Weight Gain of Lambs on Test

| | Test Conditions | | | Supplement[2] | | | | Statistics | | | | |
|---|---|---|---|---|---|---|---|---|---|---|---|---|
| | Add. | Heat | Fescue | A[1] | B | C[1] | D | Mean | SEM | Trt | Period | Per × Trt |
| Weight Gain (g/d) | | | | | | | | | | | | |
| Periods 1–2 | + | − | − | 516 | 613 | 682 | 531 | 586 | 70 | 0.82 | | |
| Period 3 | + | + | − | 594 | 442 | 312 | 760 | 527 | 108 | 0.26 | | |
| Period 4 | + | + | + | −212 | −145 | −131 | −45 | −133 | 58 | 0.86 | | |
| Overall | | | | 174 | 183 | 312 | 272 | 235 | 54 | 0.39 | <0.01 | 0.75 |
| Dry Matter Intake (g/d) | | | | | | | | | | | | |
| Period 1 | − | − | − | 710 | 654 | 647 | 492 | 626 | 69 | 0.55 | | |
| Period 2 | + | − | − | 879 | 644 | 804 | 814 | 785 | 59 | 0.71 | | |

TABLE 3-continued

Feed Intake and Weight Gain of Lambs on Test

| | Test Conditions | | | Supplement[2] | | | | Statistics | | | | |
|---|---|---|---|---|---|---|---|---|---|---|---|---|
| | Add. | Heat | Fescue | A[1] | B | C[1] | D | Mean | SEM | Trt | Period | Per × Trt |
| Period 3 | + | + | − | 890 | 743 | 863 | 1007 | 876 | 69 | 0.28 | | |
| Period 4 | + | + | + | 384 | 496 | 502 | 614 | 499 | 97 | 0.45 | | |
| Overall | | | | 626 | 582 | 648 | 691 | 637 | 79 | 0.65 | <0.01 | 0.61 |

[1]Treatment A and Treatment C each had one lamb removed during Period 4 due to poor health.
[2]Composition of supplements:
Treatment A = 100% soyhulls.
Treatment B = 50% soyhulls and 50% clay blend.
Treatment C = 49.9% soyhulls, 50% clay blend, and 0.1% capsicum product.
Treatment D = 46.4% soyhulls, 50% clay blend, 3.5% vitamin E, and 0.1% capsicum product.

TABLE 4

Indicators of Apparent Fescue Toxicity in Lambs

| | Test Conditions | | | Supplement | | | | Statistics | | | | |
|---|---|---|---|---|---|---|---|---|---|---|---|---|
| | Add. | Heat | Fescue | A[4] | B | C[4] | D | Mean | SEM | Trt | Period | Per × Trt |
| Heart Rate (bpm)[1] | | | | | | | | | | | | |
| Period 1 | − | − | − | 63 | 58 | 60 | 62 | 61 | 2.1 | 0.29 | | |
| Period 2 | + | − | − | 62 | 61 | 62 | 62 | 62 | 4.2 | 0.99 | | |
| Period 3 | + | + | − | 86 | 77 | 80 | 92 | 84 | 8.2 | 0.61 | | |
| Period 4[2] | + | + | + | 137 | 130 | 135 | 132 | 133 | 3.3 | 0.46 | | |
| Overall | | | | 87 | 82 | 84 | 87 | 85 | 2.7 | 0.50 | <0.01 | 0.93 |
| Respiration Rate (rpm) | | | | | | | | | | | | |
| Period 1 | − | − | − | 31 | 25 | 29 | 28 | 28 | 2.6 | 0.41 | | |
| Period 2 | + | − | − | 33 | 32 | 33 | 30 | 32 | 1.6 | 0.59 | | |
| Period 3[3] | + | + | − | 132 | 125 | 128 | 111 | 124 | 5.4 | 0.10 | | |
| Period 4[2,3] | + | + | + | 146 | 142 | 144 | 151 | 145 | 3.6 | 0.40 | | |
| Overall | | | | 86 | 81 | 84 | 80 | 82 | 2.8 | 0.30 | <0.01 | 0.70 |
| Rectal Temperature (° F.) | | | | | | | | | | | | |
| Period 1 | − | − | − | 102.6 | 102.8 | 102.7 | 102.6 | 102.7 | 0.3 | 0.97 | | |
| Period 2 | + | − | − | 102.7 | 102.4 | 102.4 | 102.3 | 102.4 | 0.3 | 0.79 | | |
| Period 3 | + | + | − | 103.3 | 103.3 | 103.0 | 103.0 | 103.2 | 0.3 | 0.82 | | |
| Period 4[2] | + | + | + | 105.3 | 105.0 | 105.3 | 104.9 | 105.1 | 0.1 | 0.09 | | |
| Overall | | | | 103.4 | 103.4 | 103.3 | 103.2 | 103.3 | 0.2 | 0.77 | <0.01 | 0.98 |

[1]Each period was independently analyzed.
[2]Represents the average of six repeated measurements within period 4.
[3]Respiration rates higher than 90 rpm are estimated due to lambs panting.
[4]Treatment A and Treatment C each had one lamb removed during Period 4 due to poor health.

TABLE 5

Clinical Markers of Fescue Toxicity in Lambs

| | Test Conditions | | | Supplement | | | | Statistics | | | | |
|---|---|---|---|---|---|---|---|---|---|---|---|---|
| | Add. | Heat | Fescue | A[3] | B | C[3] | D | Mean | SEM | Trt | | |
| Prolactin (ng/ml) | | | | | | | | | | | Period | Per × Trt |
| Period 1 | − | − | − | 136 | 319 | 125 | 239 | 205 | 30 | 0.28 | | |
| Period 2 | + | − | − | 387 | 295 | 556 | 325 | 391 | 30 | 0.39 | | |
| Period 3 | + | + | − | 565 | 491 | 342 | 510 | 477 | 30 | 0.38 | | |
| Period 4[1] | + | + | + | 8 | 18 | 9 | 21 | 14 | 18 | 0.25 | | |
| Overall | | | | 267 | 292 | 249 | 277 | 272 | 27 | 0.74 | <0.01 | 0.03 |
| Urinary Alkaloids (ng alk/mg creatinine)[2] | | | | | | | | | | | Day | Day × Trt |
| Obs. 1 | + | + | − | 45 | 30 | 16 | 39 | 33 | 11 | 0.71 | | |
| Obs. 2 | + | + | + | 73 | 173 | 107 | 111 | 116 | 24 | 0.58 | | |

TABLE 5-continued

Clinical Markers of Fescue Toxicity in Lambs

| | Test Conditions | | | Supplement | | | | Statistics | | |
|---|---|---|---|---|---|---|---|---|---|---|
| | Add. | Heat | Fescue | A[3] | B | C[3] | D | Mean | SEM | Trt |
| Obs. 3 | + | + | + | 147 | 168 | 147 | 187 | 162 | 65 | 0.90 | |
| Overall | + | + | + | 116 | 181 | 131 | 159 | 147 | 36 | 0.64 | 0.25 | 0.83 |

[1]Represents the average of three samples collected during Period 4. Analysis was performed using repeated measures.
[2]All alkaloid observations were made during Period 4;
Obs. 1 was made immediately prior to the consumption of ergovaline-contaminated diet.
[3]Treatment A and Treatment C each had one lamb removed during Period 4 due to poor health.

Example 2

In Vitro Screening of Ability to Bind Ergovaline

An in vitro study was performed to screen several additives for efficacy in prevention or treatment of fescue toxicosis. The screening method evaluated the ability of a bacterial product, a seaweed, a yeast and clay blend, a clay blend, and a mixture of a bacterial product and a clay blend to bind the fescue toxin, ergovaline, and prevent the production of ergot alkaloids in vitro. Fescue seed was added to an artificial rumen fermentation system and fermented for 12 or 24 hours in conjunction with test products. Fermentation was performed in a volume of 40 ml with 0.5 g of fescue seed (approximately 2000 ppb ergovaline in the seeds) (Table 6—Description of the Treatments). In order to collect enough material for analysis, six replicates of each treatment were pooled and centrifuged at the end of each treatment period. Each run (12 or 24 hours) contained all five test additives and two controls in separate fermentation vessels and was performed in duplicate. A negative control contained seed and buffers, but lacked rumen fluid inoculum and additives. The positive control contained fescue seed and rumen fluid, but no treatment was included. After fermentation and centrifugation, ergot alkaloid content of the fluid was determined, representing the soluble toxins that are easily transferred across the rumen wall. The pellet was analyzed for ergot alkaloid formation and ergovaline content. The residue collected for sample analysis was weighed and used to determine digestibility. This process was not done quantitatively; therefore, digestibility values should be regarded as estimates.

Ergot alkaloids were present in a sample of the starting fescue seed at 1543 ppb. After 12 hours of incubation, the clay blend, the yeast and clay blend, and the bacterial product/clay blend mixture treatments were able to reduce alkaloids present in rumen fluid compared to the positive control (Table 7—Ergot alkaloid and ergovaline content of fermentation systems). However, values were not different from the negative control. This suggests that clays, yeast and clay, or a mixture of a bacterial product and clay may be able to slow the rate of conversion of ergovaline to ergot alkaloids. This reduction was no longer detected at 24 hours or in the overall analysis. The addition of rumen fluid to ergovaline-contaminated fescue seed resulted in an increase in pellet ergot alkaloids. This indicates that the rumen bio-activates the poorly soluble ergovaline into alkaloids that are soluble in rumen fluid and, hence, have a greater opportunity to cross the rumen wall and induce toxicosis. Surprisingly, pellet alkaloid concentrations at 12 hours were not affected by incubation with any of the additives. At 24 hours, the positive control had higher alkaloids than the negative control in the pellet. This increase was not significantly reduced by any of the treatments. In the overall analysis, the clay blend and the bacterial product/clay blend mixture did have lower alkaloid concentrations than the positive control, indicating the ability to either slow the production of alkaloids or increase the rate of alkaloid degradation. Ergovaline concentration of the pelleted material was unaffected by any additive. This suggests that ergovaline, which is largely insoluble, was present at a similar concentration at the onset and, hence, conclusion of the incubation. Despite conversion to significant quantities of alkaloids, the majority of ergovaline remained intact.

TABLE 6

Description of Treatments

| Treatment | Rumen Fluid | Product | Amount of Product per Liter | Equivalent feeding rate |
|---|---|---|---|---|
| Negative Control | None | None | 0 | 0 |
| Positive Control | Yes | None | 0 | 0 |
| Bacterial Product | Yes | Bacterial Product | 0.61 grams | 38 grams |
| Clay Blend | Yes | Clay Blend | 0.93 grams | 56 grams |
| Seaweed | Yes | Seaweed | 10 grams | 170 grams |
| Clay and Yeast Blend | Yes | Clay and Yeast Extract Blend | 0.33 grams | 20 grams |
| Bacterial Product and Clay Blend | Yes | ½ Bacterial Product + ½ clay Blend | 0.31 g Bacterial product + 0.47 g clay blend | 19 g Bacterial product + 28 g clay blend |

TABLE 7

Ergot Alkaloid and Ergovaline Content of Fermentations

| | Negative Control | Positive Control | Bacterial Product | Clay Blend | Seaweed | Clay + Yeast Blend | Bacterial Product and Clay Blend | Mean | SEM | Trt |
|---|---|---|---|---|---|---|---|---|---|---|
| Liquid alkaloids, ppb | | | | | | | | | | |
| 12 hrs | 81[abc] | 96[ab] | 38[bcd] | 12[cd] | 39[bcd] | 22[cd] | 19[cd] | 44 | 25 | P = 0.05 |
| 24 hrs | 28 | 20 | 107 | 86 | 52 | 80 | 12 | 55 | 30 | P = 0.10 |
| Overall | 55 | 58 | 73 | 49 | 46 | 51 | 16 | 50 | 20 | P = 0.63 |

TABLE 7-continued

Ergot Alkaloid and Ergovaline Content of Fermentations

|  | Negative Control | Positive Control | Bacterial Product | Clay Blend | Seaweed | Clay + Yeast Blend | Bacterial Product and Clay Blend | Mean | SEM | Trt |
|---|---|---|---|---|---|---|---|---|---|---|
| Pellet Alkaloids, ppb |  |  |  |  |  |  |  |  |  |  |
| 12 hrs | 4932 | 6423 | 6432 | 3849 | 4296 | 5342 | 3961 | 5033 | 897 | $P = 0.11$ |
| 24 hrs | $3961^{de}$ | $10289^{ab}$ | $12050^{a}$ | $7452^{bcd}$ | $8169^{bcd}$ | $11870^{a}$ | $6369^{bcde}$ | 8594 | 2143 | $P < 0.01$ |
| Overall | $4446^{cd}$ | $8356^{abc}$ | $9241^{ab}$ | $5650^{cd}$ | $6233^{bcd}$ | $8606^{ab}$ | $5165^{cd}$ | 6814 | 1457 | $P < 0.01$ |
| Pellet ergovaline, ppb |  |  |  |  |  |  |  |  |  |  |
| 12 hrs | 1085 | 1250 | 1243 | 1205 | 1268 | 1343 | 1255 | 1236 | 81 | $P = 0.55$ |
| 24 hrs | 1185 | 1605 | 1295 | 1640 | 1145 | 1640 | 1672 | 1455 | 226 | $P = 0.21$ |
| Overall | 1135 | 1428 | 1269 | 1423 | 1206 | 1491 | 1464 | 1345 | 130 | $P = 0.11$ |
| Digestibility (%)[1] |  |  |  |  |  |  |  |  |  |  |
| 12 hrs | 58 | 58 | 51 | 52 | 49 | 57 | 53 | 54 | 0.07 | $P = 0.46$ |
| 24 hrs | $73^{cd}$ | $70^{bcd}$ | $68^{bcd}$ | $68^{bcd}$ | $57^{ab}$ | $66^{abcd}$ | $61^{abc}$ | 66 | 0.05 | $P = 0.06$ |
| Overall | $65^{cd}$ | $64^{cd}$ | $60^{bcd}$ | $60^{bcd}$ | $53^{ab}$ | $62^{bcd}$ | $57^{abc}$ | 60 | 0.05 | $P = 0.01$ |

$abcde$ = Treatments with different superscripts differ P greater than 0.05. Any values with the same superscript in a row are not statistically different.
[1]Estimated, Dry matter was not quantitatively recovered.

Example 3

Palatability Evaluation of Composition

In this Example, the palatability of two different forms of non-limiting embodiments of the composition of the present disclosure was evaluated. Both forms, a loose meal and tub, were consumed by the cattle at desirable levels.

In a first trial, fourteen pregnant Holstein heifers, average weight 525 kg, were randomly allotted to two six-acre grass lots. Each lot contained two mineral feeders. PROSPECTOR® 15-7 Fescue Mineral (available from ADM Alliance Nutrition Inc of Quincy Ill., ingredients listed in Table 8) was offered in one feeder and a loose form of a fescue mineral composition was offered in the other (Table 8—Compositions of mineral mixes). Weekly mineral disappearance was monitored and feeders were moved on a weekly basis. FIG. 1 is a graphical comparison of the amount of consumption of the two feed compositions. Average body weight increased by 4 kg over the course of the three-week study and body temperature at the conclusion was 101.7° F., indicating that the cattle were generally healthy and not undergoing fescue toxicity. Two different statistical methods were used to analyze the intake data. Repeated measurements and analysis assessed whether actual intake of the two mineral products differed. Intake of the test formulation was significantly greater than that of a currently offered fescue mineral (0.11 vs. 0.04 kg/head/day). Three weeks of intake data from two pens gave six observations, where the cattle tended to prefer the new product (by a ratio of 5 to 1). Target intake of PROSPECTOR® mineral was 4 oz./head/day. The inclusion of a composition according to one embodiment of the present disclosure with the base mineral increased target intake of the new mineral to 8 oz./head/day. While neither mineral was consumed at the target level, the test product consumption was 2.75 times greater than that of the PROSPECTOR® mineral.

Figure 2:
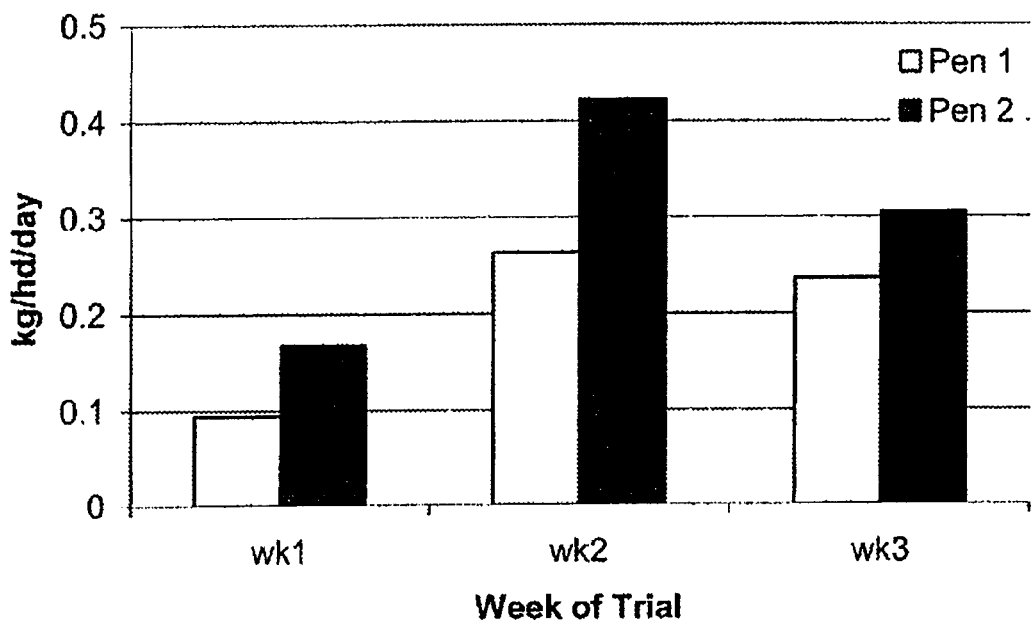
FIG. 2 is a graph showing consumption of one composition according to a non-limiting embodiments disclosed herein in tub form compared to a commercially available tub feed composition.

In a second trial, two 250-pound pressed tubs were created. Two pastures containing 14 head per pasture were used to evaluate the intake of the animal feed composition in the pressed tub. One tub was placed in each lot, the weight of the tub was determined on a weekly basis, and disappearance was attributed to consumption by the cattle. The addition of ingredients needed to make a high quality tub resulted in a target intake of 8 oz./head/day (0.23 Kg). Consumption values for the pressed tubs are presented in FIG. 2. Initial observations indicated that the tubs were extremely hard. Intake was below target during the first week. However, high rainfall and the high palatability of the tubs led to an increase in intake for weeks 2 and 3. Overall intake was 8.8 oz./head/day (0.25 kg).

In the two sensory evaluations, formulations containing compositions according to one embodiment of the present disclosure were well tolerated and consumed at an adequate level. The fescue mineral comprising embodiments of the present disclosure were preferred to the PROSPECTOR® mineral by dairy heifers on pasture. Pelleting of this formulation may produce a commercially acceptable product. In another embodiment, the free form of the compositions of the present disclosure without mineral may be used during feed manufacture. The fescue mineral tubs comprising compositions according to various embodiments of the present disclosure may be used for cattle on pasture that receive no additional supplementation.

TABLE 8

Composition of Mineral Mixes

|  | Prospector | Fescue Mineral (Loose) | Fescue Mineral (Tub) |
|---|---|---|---|
| INGREDIENTS (percent by weight) |  |  |  |
| CO-DRIED BREWERS YEAST | 2.000 | 0.991 | — |
| SOYHULLS | 5.817 | 2.883 | — |
| MOLASSES | — | — | 25.000 |
| CALCIUM CARBONATE 38 | 25.503 | 12.639 | 6.650 |
| PHOS MONOCAL 21 | 33.222 | 16.464 | 18.188 |
| SALT | 19.388 | 9.608 | 4.100 |
| VITAMIN AND MINERAL BLEND | 12.07 | 5.983 | 7.142 |
| GREASE MX CHOICE WHITE | 2.000 | 0.991 | — |
| DISTILLERS | — | — | 0.550 |

TABLE 8-continued

Composition of Mineral Mixes

| | Prospector | Fescue Mineral (Loose) | Fescue Mineral (Tub) |
|---|---|---|---|
| NUTRADE (ALUMINOSILICATE CLAY) | — | 24.780 | 12.500 |
| NUTREON (VITAMIN E) | — | 0.874 | 0.870 |
| YEAST CREAM DRIED | — | 24.780 | 25.000 |
| CAPSICUM PRODUCT | — | 0.007 | — |
| TOTAL NUTRIENTS | 100.000 | 100.000 | 100.000 |
| CALCIUM, % | 16.29 | 8.16 | 6.56 |
| PHOSPHORUS, % | 7.13 | 3.62 | 4.39 |
| SALT, % | 19.35 | 9.65 | 4.40 |
| SODIUM, % | 7.76 | 3.92 | 1.87 |
| CHLORIDE, % | 12.48 | 6.23 | 3.28 |

Example 4

Palatability Evaluation of Capsicum Comprising Composition

This Example showed that inclusion of the capsicum product in the feed composition had little to no affect on the voluntary feed intake. Capsicum product was included in diets at 15 mg/head/day and 150 mg/head/day. It was also shown that consumption of the capsicum product had an effect on core body temperature, as measured by the rectal temperature (RT), and vasodilation. Vasodilation was assessed by using an infrared thermometer to determine ear temperature (ET), hoof temperature (HT), and surface body temperature (BT). All temperature measurements are reported in ° F. in this Example.

Cattle were divided into 9 pastures of 11-12 head/pasture with three treatments across three weight/gender blocks (heavy steers, heavy heifers, and light mixed steers/heifers). Each pasture contained a small amount of shade. One group from each weight/gender block received each dietary treatment for the duration of the 8-week trial. Diets were formulated from ROUGH-N-READY™ 14 product (available from ADM Alliance Nutrition Inc. of Quincy, Ill.) (Table 9—Ingredients and nutrition composition of supplements). Based upon a target intake of 3.15 kg/head/day, the three treatments offered included: 0 mg (BGP-6594), 15 mg (BGP-6595), or 150 mg (BGP-6596) capsicum product/day. Initially, 3.15 kg of feed per head per day was provided on a daily basis. This amount was increased to 3.79 kg/head/day at 3 weeks and 4.01 kg/head/day at 5 weeks. Mixed fescue pasture constituted the remainder of the diet. Ergovaline was present in the pasture at 110 ppb, a low level, wherein signs of toxicosis are readily apparent above 600 ppb. High temperature during the trial was 84° F. and the low was 23° F.

Body weight, RT, ET, HT, and BT were collected on days 1, 21, 42, and 57 of the trial. Performance was similar among treatments (Table 10—Performance by cattle fed the capsicum product). Weight gain was different at day 42 with cattle on the 15-mg treatment weighing less than the other two treatments. However, weight was not different at the next time point. Otherwise, no differences in body weight, total gain, average daily gain, average daily feed intake, or gain/feed ratio were observed among the treatment groups. This indicates that the capsicum product at these levels had no negative or positive effects on animal performance.

Figure 3:
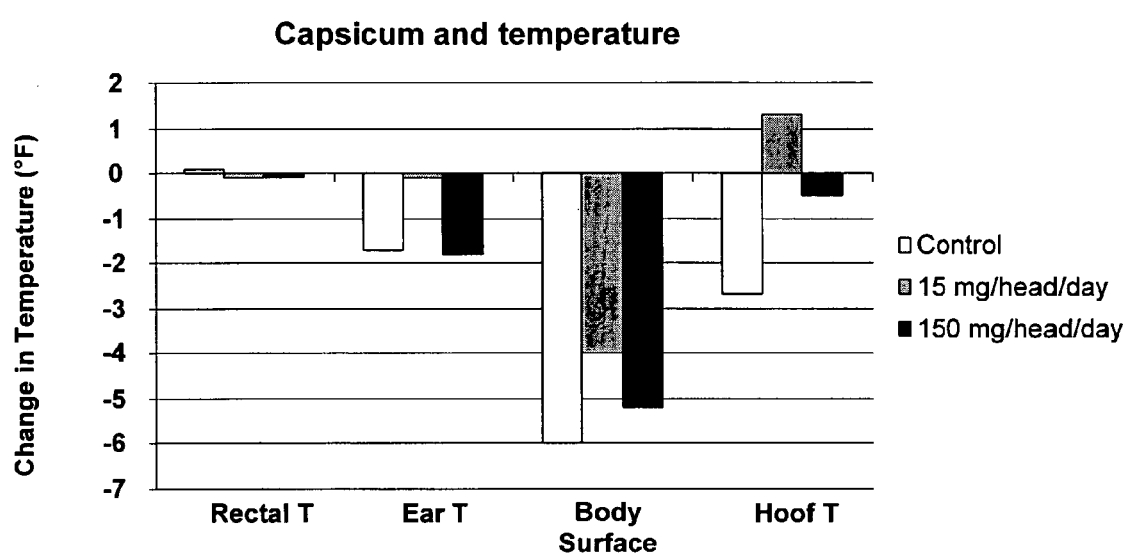
FIG. 3 is a graph showing changes in rectal, ear, body surface and hoof temperature for animals consuming compositions according to one embodiment of the present disclosure comprising capsicum compared to a control composition.

Consumption of the capsicum product altered core (RT) and peripheral temperatures (ET, HT, BT) (Table 11—Temperature values of cattle fed capsicum). Rectal temperature numerically decreased 0.1° F. in cattle consuming capsicum and increased 0.1° F. in cattle with no treatment. The small change in RT indicates that little fescue toxicosis was encountered during the trial. Overall, control cattle experienced a reduction in ear, body, and hoof temperature and an increase in rectal temperature. This observation is consistent with vasoconstriction and a reduced ability to dissipate heat. The addition of the capsicum product to the diet at 15 mg (BGP-6595) improved blood flow to the ear, body surface, and hoof (P=0.23, 0.01, and 0.04; respectively) and led to a slight numerical reduction in rectal temperature (P=0.15). Change in temperature from trial initiation and after 8 weeks of feeding is shown in FIG. 3.

Based upon the observations in this Example, the capsicum product is well tolerated in the supplement for grazing beef cattle, had no effect on the performance of healthy cattle, and may have beneficial effects on thermoregulation in cattle under moderate heat stress and/or fescue toxicosis.

TABLE 9

Ingredient and Nutrient Composition of Supplements

| | BGP6594 | | BGP6595 | | BGP6596 | |
|---|---|---|---|---|---|---|
| INGREDIENTS, (percent by weight) | | | | | | |
| Soyhulls | 49.00 | | 49.00 | | 49.00 | |
| Corn Gluten Feed | 25.00 | | 25.00 | | 25.00 | |
| Wheat Middlings | 14.39 | | 14.38 | | 14.38 | |
| Molasses-Cane | 4.00 | | 4.00 | | 4.00 | |
| Calcium Carbonate 38 | 3.48 | | 3.48 | | 3.48 | |
| Arsoy-Soybean Feed | 2.96 | | 2.97 | | 2.97 | |
| Salt | 1.02 | | 1.02 | | 1.02 | |
| Mineral And Vitamin Blend | 0.15 | | 0.15 | | 0.15 | |
| Capsicum Product | — | | 0.0016 | | 0.0047 | |
| TOTAL NUTRIENTS | 100.00 | | 100.00 | | 100.00 | |
| Dry Matter (%) | 89.95 | | 89.95 | | 89.95 | |
| Moisture (%) | 10.05 | (9.85)[1] | 10.05 | (9.10) | 10.05 | (9.65) |
| Protein (%) | 15.56 | (15.64) | 15.56 | (15.57) | 15.56 | (15.55) |
| Fat; Crude (%) | 2.24 | (2.22) | 2.24 | (2.15) | 2.24 | (2.22) |
| Crude Fiber (%) | 24.14 | | 24.14 | | 24.14 | |

TABLE 9-continued

Ingredient and Nutrient Composition of Supplements

|  | BGP6594 |  | BGP6595 |  | BGP6596 |  |
|---|---|---|---|---|---|---|
| Calcium (%) | 1.95 | (1.78) | 1.95 | (1.65) | 1.95 | (1.72) |
| Phosphorus (%) | 0.49 | (0.44) | 0.49 | (0.45) | 0.49 | (0.44) |
| Net Energy Gain (mcal/lb) | 0.53 | | 0.53 | | 0.53 | |
| Vitamin E (iu/lb) | 16.66 | | 16.66 | | 16.66 | |

[1] Analyzed values in parentheses.

TABLE 10

Performance by Cattle Fed Capsicum Product

| | Treatment | | | | | |
| | 1 | 2 | 3 | | | |
| | Capsicum (mg/hd/d) | | | | | Trt |
| | 0 | 15 | 150 | Mean | SEM | P Value |
| Weight, kg | | | | | | TRT |
| Day 1 | 316.5 | 308.8 | 309.9 | | | |
| Day 21 | 353.5 | 346.2 | 346.6 | 348.8 | 3.0 | 0.28 |
| Day 42 | 368.8 | 354.3 | 363.1 | 362.1 | 1.3 | <0.01 |
| Day 57 | 378.7 | 367.9 | 370.2 | 372.2 | 3.6 | 0.20 |
| Total Gain, kg/hd | | | | | | |
| Day 1–21 | 37.0 | 37.5 | 36.7 | 37.1 | 1.9 | 0.96 |
| Day 22–42 | 15.3 | 8.0 | 16.5 | 13.3 | 3.7 | 0.33 |
| Day 43–57 | 9.9 | 13.6 | 7.1 | 10.2 | 4.3 | 0.60 |
| Overall | 62.2 | 59.1 | 60.2 | 60.5 | 3.3 | 0.81 |
| Average Daily Gain, kg/hd/d | | | | | | |
| Day 1–21 | 1.76 | 1.78 | 1.75 | 1.76 | 0.09 | 0.96 |
| Day 22–42 | 0.73 | 0.38 | 0.78 | 0.63 | 0.18 | 0.33 |
| Day 43–57 | 0.71 | 0.97 | 0.50 | 0.73 | 0.30 | 0.60 |
| Overall | 1.11 | 1.06 | 1.08 | 1.08 | 0.06 | 0.81 |
| Average Daily Feed Intake, kg/hd/d | | | | | | |
| Day 1–21 | 1.43 | 1.43 | 1.43 | 1.43 | 0.01 | 0.44 |
| Day 22–42 | 1.72 | 1.72 | 1.72 | 1.72 | 0.00 | 1.00* |
| Day 43–57 | 1.82 | 1.82 | 1.82 | 1.82 | 0.00 | 1.00* |
| Overall | 1.64 | 1.64 | 1.64 | 1.64 | 0.004 | 0.44 |
| Gain/Feed, × 100 | | | | | | |
| Day 1–21 | 25.4 | 25.7 | 25.2 | 25.4 | 1.3 | 0.97 |
| Day 22–42 | 8.8 | 4.6 | 9.4 | 7.6 | 2.1 | 0.33 |
| Day 43–57 | 7.8 | 10.8 | 5.6 | 8.1 | 3.4 | 0.60 |
| Overall | 13.9 | 13.2 | 13.5 | 13.5 | 0.7 | 0.80 |

*Cattle rapidly consumed all feed offered.

TABLE 11

Temperature of Cattle Fed Capsicum Product

| | Treatment | | | | | Trt P Value | | | |
| | 1 | 2 | 3 | | | | | | |
| | Capsicum (mg/hd/d) | | | | | | | | |
| | 0 | 15 | 150 | Mean | SEM | All | 1 vs. 2 | 1 vs. 3 | 2 vs. 3 |
| Rectal Temperature, °F. | | | | | | | | | |
| Period 1 | 103.0 | 103.3 | 103.1 | 103.1 | 0.13 | 0.36 | 0.20 | 0.94 | 0.23 |
| Period 2 | 103.5 | 103.9 | 103.4 | 103.6 | 0.15 | 0.05 | 0.09 | 0.47 | 0.02 |
| Period 3 | 102.7 | 102.6 | 102.7 | 102.7 | 0.11 | 0.70 | 0.49 | 0.94 | 0.45 |
| Overall | 103.1 | 103.2 | 103.0 | 103.1 | 0.74 | 0.16 | 0.15 | 0.70 | 0.07 |
| Ear Temperature, °F. | | | | | | | | | |
| Period 1 | 85.3 | 84.7 | 86.3 | 85.4 | 0.85 | 0.38 | 0.58 | 0.41 | 0.17 |
| Period 2 | 84.6 | 87.7 | 86.1 | 86.2 | 0.95 | 0.06 | 0.02 | 0.24 | 0.22 |
| Period 3 | 81.0 | 81.5 | 81.1 | 81.2 | 1.06 | 0.94 | 0.73 | 0.92 | 0.81 |
| Overall | 83.6 | 84.6 | 84.5 | 84.3 | 0.58 | 0.41 | 0.23 | 0.27 | 0.92 |
| Body Temperature, °F. | | | | | | | | | |
| Period 1 | 81.8 | 81.1 | 81.4 | 81.4 | 0.49 | 0.61 | 0.33 | 0.54 | 0.72 |
| Period 2 | 78.1 | 80.8 | 78.6 | 79.2 | 0.70 | 0.02 | 0.01 | 0.62 | 0.03 |
| Period 3 | 67.4 | 69.5 | 68.6 | 68.5 | 0.61 | 0.05 | 0.02 | 0.15 | 0.32 |
| Overall | 75.8 | 77.1 | 76.2 | 76.4 | 0.37 | 0.03 | 0.01 | 0.40 | 0.08 |
| Hoof Temperature, °F. | | | | | | | | | |
| Period 1 | 74.8 | 69.7 | 71.8 | 72.1 | 0.65 | 0.001 | 0.001 | 0.001 | 0.02 |
| Period 2 | 74.4 | 76.2 | 74.0 | 74.9 | 0.67 | 0.04 | 0.05 | 0.67 | 0.02 |
| Period 3 | 67.2 | 67.1 | 68.1 | 67.5 | 0.71 | 0.55 | 0.92 | 0.37 | 0.32 |
| Overall | 72.1 | 71.0 | 71.3 | 71.5 | 0.39 | 0.11 | 0.04 | 0.13 | 0.62 |

Example 5

Weight Study of Cattle Consuming Supplement

This Example assessed the performance and intake levels of one non-limiting embodiment of the compositions of the present disclosure. This Example also evaluated a complete mineral formulation containing one embodiment of a composition of the present disclosure compared to a complete mineral formulation without supplementation. The embodiment of the composition of the present disclosure was blended with a mineral base of MASTERGAIN® 16/8 mineral (available from ADM Alliance Nutrition Inc. of Quincy, Ill.) and compared against a control mineral consisting of the MASTERGAIN® 16/8 mineral blend without supplementation (see Table 12—Composition of mineral supplements).

Beef cattle consuming endophyte-infected fescue were used. Two pastures, a control pasture and a study pasture, located on the same farm were used. The control pasture contained 29 cows and 22 calves, while the study pasture contained 26 cows and 26 calves. Cattle in the control pasture were offered the control mineral, with a target intake of 113.5 grams/head/day. Cattle in the study pasture were offered the blend of the supplement and mineral base, with a target intake of 141.9 grams/head/day. Both minerals were well consumed at approximately twice the target feeding rate (see Table 13—Growth of cattle consuming control and supplemented mineral preparations). Calculations were based on the assumption that only the cows were consuming the mineral. Likely, the calves consumed some amount of the mineral as well.

As shown in Table 13, cattle that consumed endophyte-infected fescue in the control pasture lost weight during the trial (−10.8 kg/head on average), while the cattle that consumed endophyte-infected fescue in the study pasture gained weight (+11.4 kg/head on average). Similar results were observed with the calves. Calves in the study pasture were lighter at the start of the trial and ended the trial heavier than calves in the control pasture. Calves in the study pasture gained 40% more weight over the course of the trial, equating to a 260 grams/head/day improvement in weight gain. Of special note is the observation that the cows in the study pasture gained weight and also raised a heavier set of calves, while the cows in the control pasture lost weight and their calves had reduced performance.

TABLE 12

Composition of Mineral Supplements

| | Unit | BLM6628 | BLM6629 | BLP6630[1] |
|---|---|---|---|---|
| INGREDIENTS, (percent by weight) | | | | |
| BLP6630 | | — | 30.00 | — |
| MONOCAL 21% COARSE | | 37.94 | 18.79 | — |
| LIMESTONE | | 26.50 | 12.40 | — |
| SALT | | 15.47 | 18.56 | — |
| MOLASSES-CANE | | 2.00 | — | 10.00 |
| CHLORMAX-50 (CHLORTETRACYCLINE) | | 2.80 | 2.24 | — |
| VIT E | | 0.07 | — | 1.89 |
| ALUMINOSILICATE CLAY | | — | — | 8.35 |
| DISTILLERS GRAINS | | — | 4.60 | 8.27 |
| PROSPONSE M (CO-DRIED CITRIC ACID PRESSCAKE) | | — | — | 66.70 |
| VITAMIN AND MINERAL BLEND | | 15.22 | 13.41 | 4.72 |
| CAPSICUM PRODUCT | | — | — | 0.07 |
| TOTAL | | 100.00 | 100.00 | 100.00 |
| NUTRIENTS | | | | |
| PROTEIN | % | 2.07 | 3.37 | 3.26 |
| FAT; CRUDE | % | 2.68 | 3.27 | 0.23 |
| CRUDE FIBER | % | 0.31 | 0.57 | 0.60 |
| DRY MATTER | % | 98.17 | 97.37 | 96.77 |
| NET ENERGY GAIN | MC/LB | 0.03 | 0.06 | 0.09 |
| CALCIUM | % | 16.41 | 7.99 | 0.09 |
| PHOSPHORUS | % | 7.99 | 4.03 | 0.07 |
| VITAMIN E | IU/LB | 151.37 | 1284.48 | 4424.29 |

[1]BLP6630 is the experimental supplement. This blend was mixed into a mineral base to give BLM6629 for delivery to the animal. BLM6629 contained 30% of the experimental supplement.

TABLE 13

Growth Of Cattle Consuming Control And Study Mineral Preparations

| | Control | Study |
|---|---|---|
| Cow data | | |
| Starting weight (kg) | 506.4 | 489.5 |
| Ending weight (kg) | 495.6 | 500.9 |
| Weight change (kg) | −10.8 | +11.4 |
| Average daily gain (grams) | −110 | +110 |
| Average daily feed intake (grams) | 250 | 277 |
| Calf data | | |
| Starting weight (kg) | 125.0 | 121.8 |
| Ending weight (kg) | 190.6 | 213.6 |
| Weight change (kg) | +65.6 | +91.8 |
| Average daily gain (grams) | +660 | +920 |

Example 6

Animal Feed Composition

This Example illustrates one embodiment of an animal feed composition useful for treating symptoms associated with a fescue toxicosis condition in cattle or other fescue consuming animals. The feed composition ingredients are presented in Table 14.

The ingredients were mixed together to form an animal feed composition in the form of a feed supplement and placed in a container, such as a bag. The bag had indicia directing how the animal feed composition should be administered to animals and/or recommended amounts of the animal feed composition to be provided to the animals. According to this Example, the animal feed composition was configured to be provided to animals in a free choice manner, wherein the animal feed composition is placed in proximity to the animals such that the animals can consume the animal feed composition at will. According to one embodiment, the indicia was configured to direct a rancher to provide the animal feed composition at a rate of about 4 ounces per day per animal. Under these conditions, each animal received a dose of about 30 mg of the coated capsicum (i.e., the vasodilator) per day in order to alleviate the effects of fescue toxicity. In other embodiments, the indicia may be configured to instruct the user to provide the animal feed composition in amounts sufficient to provide from about 10 mg of coated capsicum per day per animal to about 500 mg coated capsicum per day per animal.

TABLE 14

Animal Feed Composition

| Ingredient | Percentage (%) by weight of Animal Feed Composition |
|---|---|
| Minerals | 57.22 |
| Salt | 18.23 |
| Distillers dried grains | 8.10 |
| Spray dried yeast product | 6.17 |
| Adsorbent clay (aluminum silicate) | 3.52 |
| Petrolatum | 3.00 |
| Molasses (cane) | 2.00 |
| Vitamin E, 227 KIU/lb | 1.15 |
| Trace minerals and vitamins | 0.58 |
| Vasodilator (coated capsicum) | 0.03 |

Other embodiments of the animal feed compositions may include a co-dried yeast product as a carrier, such as PROSPONSE® (a registered trademark of ADM Alliance Nutrition Inc., Quincy, Ill.); potassium sulfate; cobalt carbonate; ferrous sulfate; a flavoring, such as, for example, caramel flavor; various vitamins or trace minerals; mineral oil; molasses, which may be dried; and any combination thereof.

Example 7

Animal Feed Composition

This Example illustrates another embodiment of an animal feed composition useful for treating symptoms associated with a fescue toxicosis condition in cattle or other fescue consuming animals. The feed composition ingredients are presented in Table 15.

TABLE 15

Animal Feed Composition

| Ingredient | Percentage (%) by weight of Animal Feed Composition |
|---|---|
| Minerals | 57.15 |
| Salt | 18.23 |
| Distillers dried grains | 4.20 |
| Spray dried yeast product | 6.17 |
| Adsorbent clay (aluminum silicate) | 3.52 |
| Petrolatum | 3.00 |
| Chloratet 50 (an antibiotic) | 2.80 |
| Molasses (cane) | 2.00 |
| Methoprine (insect growth regulator) | 1.17 |
| Vitamin E, 227 KIU/lb | 1.15 |
| Trace minerals and vitamins | 0.58 |
| Vasodilator (coated capsicum) | 0.03 |

The ingredients were mixed together to form an animal feed composition in the form of a feed supplement and placed in a container, such as a bag. The bag had indicia directing how the animal feed composition should be administered to animals and/or recommended amounts of the animal feed composition to be provided to the animals. According to this Example, the animal feed composition was configured to be provided to animals in a free choice manner, wherein the animal feed composition is placed in proximity to the animals such that the animals can consume the animal feed composition at will. According to one embodiment, the indicia was configured to direct a rancher to provide the animal feed composition at a rate of about 4 ounces per day per animal. Under these conditions, each animal received a dose of about 30 mg of the coated capsicum (i.e., the vasodilator) per day in order to alleviate the effects of fescue toxicity. In other embodiments, the indicia may be configured to instruct the user to provide the animal feed composition in amounts sufficient to provide from about 10 mg of coated capsicum per day per animal to about 500 mg coated capsicum per day per animal.

Other embodiments of the animal feed composition may include a co-dried yeast product as a carrier, such as PROSPONSE®; potassium sulfate; cobalt carbonate; ferrous sulfate; a flavoring, such as, for example, caramel flavor; other antibiotics, such as, but not limited to CTC (chlorotetracycline) 100, aureomycin 100, CTC 90, aureomycin 90, pennchlor 100, pennchlor 70, aureomycin 70, chlormax 50, pennchlor 50, and aureomycin 50; various vitamins or trace minerals; mineral oil; molasses, which may be dried; and any combination thereof.

Example 8

Animal Feed Supplement

According to this Example, an animal feed supplement useful for treating symptoms associated with a fescue toxicosis condition includes the following ingredients. An amount of the animal feed supplement may be admixed with feed matter to dilute the concentrations of ingredients in the supplements such that, upon feeding to an animal, the animal receives an effective amount of each ingredient by consuming the feed matter admixed with the animal feed supplement. Table 16 lists the ingredients of the animal feed supplement. CITRISTIM® is a commercially available *Pichia guilliermondii*, citric acid fermentation culture available from Archer Daniels Midland Co. of Decatur, Ill.; NUTRADE® comprises Hydrated Sodium Calcium Aluminosilicate, Natural and Artificial Flavors and is available from ADM Alliance Nutrition of Quincy, Ill.; and ZINPRO AVAILA® 4 comprises an amino acid mineral complex available from ZinPro Corporation, Eden Prairie, Minn.

TABLE 16

Animal Feed Supplement

| Ingredient | Percentage (%) by weight of Animal Feed Composition |
|---|---|
| CITRISTIM ® | 45.65 |
| NUTRADE ® | 26.10 |
| ZINPRO AVAILA 4 ® | 19.55 |
| VITAMIN E, 227 KIU/lb | 8.50 |
| CAPSICUM (coated) | 0.20 |

The ingredients were mixed together to form an animal feed supplement and placed in a container, such as a bag. The bag had indicia directing how the animal feed supplement should be mixed with a feed matter and/or recommended amounts of the animal feed supplement to be provided to the animals. According to this Example, the animal feed composition was configured to be provided to animals by mixing with feed matter. According to one embodiment, the indicia was configured to direct a rancher to provide the animal feed supplement/feed matter mix that provides a dose of about 30 mg of the coated capsicum (i.e., the vasodilator) per day in order to alleviate the effects of fescue toxicity. In other embodiments, the indicia may be configured to instruct the user to provide the animal feed supplement/feed matter in amounts sufficient to provide from about 10 mg of coated capsicum per day per animal to about 500 mg coated capsicum per day per animal.

Although the foregoing description has presented a number of embodiments of the invention, those of ordinary skill in the relevant art will appreciate that various changes in the components, details, materials, and process parameters of the examples that have been herein described and illustrated in order to explain the nature of the invention may be made by those skilled in the art, and all such modifications will remain within the principle and scope of the invention as expressed herein in the appended claims. It will also be appreciated by those skilled in the art that changes could be made to the embodiments described above without departing from the broad inventive concept thereof. It is understood, therefore, that this invention is not limited to the particular embodiments disclosed, but it is intended to cover modifications that are within the principle and scope of the invention, as defined by the claims.

We claim:

1. A method for improving weight gain in an animal that has consumed an endophytic fungus comprising:
    mixing an effective amount of a capsaicin containing product with a mineral clay for adsorbing aflatoxin, ergovaline, or ergot alkaloids and a citric acid yeast culture presscake, thus producing an animal feed composition or animal feed supplement; and
    feeding the animal feed composition or animal feed supplement to an animal that has consumed the endophytic fungus, the animal being selected from the group consisting of bovines, equines, ovines, and caprines such that the animal gains weight.

2. The method of claim 1, wherein the mineral clay is aluminosilicate clay and the capsaicin containing product is capsicum.

3. The method of claim 1, wherein the capsaicin containing product is coated or encapsulated.

4. The method of claim 1, wherein the animal is afflicted with a fescue toxicosis condition or located in an environment associated with fescue toxicosis.

5. The method of claim 1 further comprising mixing an oligosaccharide source selected from the group consisting of a yeast product, a yeast culture, a yeast culture presscake, a citric acid yeast culture presscake, an ethanol yeast culture presscake, a spray dried yeast culture, a spray dried bacterial culture, a yeast extract, a modified yeast extract, a yeast enzyme, a bacterial enzyme, and combinations of any thereof with the animal feed composition or the animal feed supplement.

6. A method of improving weight gain in a bovine that has consumed an endophytic fungus comprising:
    mixing an effective amount of a capsaicin containing product with a mineral clay for adsorbing aflatoxin, ergovaline, or ergot alkaloids and a citric acid yeast culture presscake, thus producing an animal feed composition or animal feed supplement; and
    feeding the animal feed composition or the animal feed supplement to the bovine, wherein the bovine gains weight.

7. The method of claim 6, further comprising mixing a polyalcohol with the animal feed composition or the animal feed supplement.

8. The method of claim 1, wherein the animal feed composition or animal feed supplement is consumed in an amount ranging from about 10 g/head/day to about 454 g/head/day.

9. The method of claim 1, further comprising mixing polyalcohols with the animal feed composition or the animal feed supplement.

10. The method of claim 6, further comprising mixing the capsaicin containing product, the mineral clay, and the citric acid yeast culture presscake with an animal feed product selected from the group consisting of feed matter, a mineral, a vitamin, an amino acid, an antibiotic, a plant extract, a plant botanical, and combinations of any thereof.

11. The method of claim 6, wherein the bovine is under heat stress.

12. The method of claim 6, wherein the capsaicin containing product is coated or encapsulated.

13. The method of claim 1, wherein the capsaicin containing product is synthetic, isolated, extracted, or combinations of any thereof.

14. The method of claim 6, wherein the capsaicin containing product is synthetic, isolated, extracted, or combinations of any thereof.

15. The method of claim 1, wherein the endophytic fungus is *Neotyphodium coenophialum*.

16. The method of claim 1, further comprising mixing an insect growth regulator with the animal feed composition or the animal feed supplement.

17. The method of claim 6, further comprising mixing an insect growth regulator with the animal feed composition or the animal feed supplement.

18. The method of claim 1, wherein the capsaicin containing product is fed to the animal at an amount of between 10 mg to 500 mg per day.

19. The method of claim 6, wherein the capsaicin containing product is fed to the bovine at an amount of between 10 mg to 500 mg per day.

20. The method of claim 1, further comprising mixing cinnamaldehyde with the animal feed product.

21. The method of claim 1, further comprising mixing eugenol with the animal feed product.

22. The method of claim 6, wherein the capsaicin containing product is capsicum and the mineral clay is aluminosilicate clay.

23. The method of claim 1, wherein the effective amount of the capsaicin containing product is between about 0.005% to about 1.0% by weight of the animal feed composition or the animal feed supplement.

24. The method of claim 6, wherein the effective amount of the capsaicin containing product is between about 0.005% to about 1.0% by weight of the animal feed composition or the animal feed supplement.

* * * * *